US011058768B2

(12) United States Patent
Chandramouli et al.

(10) Patent No.: US 11,058,768 B2
(45) Date of Patent: Jul. 13, 2021

(54) STABLE PROTEIN FORMULATIONS COMPRISING A MOLAR EXCESS OF SORBITOL

(71) Applicants: BIOCON LTD., Bangalore (IN); MYLAN GMBH, Zurich (CH)

(72) Inventors: Kala Chandramouli, Bangalore (IN); Rohan Pai, Nipani (IN)

(73) Assignees: BIOCON LTD.; MYLAN GMBH

( * ) Notice: Subject to any disclaimer, the term of this patent is extended or adjusted under 35 U.S.C. 154(b) by 158 days.

(21) Appl. No.: 15/303,881

(22) PCT Filed: Apr. 16, 2015

(86) PCT No.: PCT/IB2015/052789
§ 371 (c)(1),
(2) Date: Oct. 13, 2016

(87) PCT Pub. No.: WO2015/159254
PCT Pub. Date: Oct. 22, 2015

(65) Prior Publication Data
US 2017/0028063 A1  Feb. 2, 2017

(30) Foreign Application Priority Data

Apr. 16, 2014 (IN) .......................... 1989/CHE/2014

(51) Int. Cl.
| *A61K 39/395* | (2006.01) |
| *C07K 16/32* | (2006.01) |
| *A61K 9/19* | (2006.01) |
| *A61K 47/26* | (2006.01) |
| *A61K 47/10* | (2017.01) |
| *A61K 47/20* | (2006.01) |
| *A61J 1/20* | (2006.01) |
| *A61J 1/06* | (2006.01) |
| *A61J 1/14* | (2006.01) |
| *A61K 47/18* | (2017.01) |
| *A61K 9/00* | (2006.01) |

(52) U.S. Cl.
CPC .......... *A61K 39/39591* (2013.01); *A61J 1/06* (2013.01); *A61J 1/1412* (2013.01); *A61J 1/2006* (2015.05); *A61K 9/19* (2013.01); *A61K 47/10* (2013.01); *A61K 47/183* (2013.01); *A61K 47/20* (2013.01); *A61K 47/26* (2013.01); *C07K 16/32* (2013.01); *A61K 9/0019* (2013.01); *C07K 2317/24* (2013.01)

(58) Field of Classification Search
CPC combination set(s) only.
See application file for complete search history.

(56) References Cited

U.S. PATENT DOCUMENTS

| 6,685,940 B2* | 2/2004 | Andya | A61K 39/39591 422/40 |
| 2008/0200655 A1* | 8/2008 | Sek | A61K 9/19 530/390.5 |
| 2012/0014968 A1* | 1/2012 | Walsh | C07K 16/22 424/158.1 |
| 2013/0287770 A1* | 10/2013 | Moretta | C07K 16/2803 424/133.1 |

FOREIGN PATENT DOCUMENTS

| WO | 2008/031531 A1 | 3/2008 |
| WO | 2009/015345 A1 | 1/2009 |
| WO | 2011/119487 A2 | 9/2011 |
| WO | WO 2011/119487 | * 9/2011 |
| WO | WO 2012151248 | * 11/2012 |

OTHER PUBLICATIONS

Prestrelski et al (Archives of Biochemistry and Biophysics, 1993, 303:465-473).*
Izutsu et al (Biotechnology and Bioengineering, 1994, 43:1102-1107).*
Schersch (Dissertation zur Erlangung des Doktorgrades der Fakultat fur Chemie und Pharmazie der Ludwig-Maximilians-Universitat Munchen, 2009).*
Drugbank trastuzumab, printed Jan. 2018.*
Mueller et al (Applied Biochemistry Biotechnology, 2013, 169:1431-1448).*
Patel et al (BioProcess International, Jan. 1, 2011; 9:20-31).*
Lam et al (Journal of Pharmaceutical Sciences, 1997, 86:1250-1255).*
Anonymous (Edited by: Ashok Katdare): "Excipient Development for Pharmaceutical, Biotechnology, and Drug Delivery Systems", 2006, CRC Press, pp. 295-300.
Wei Wang: "Lyophilization and development of solid protein pharmaceuticals", International Journal of Pharmaceutics, vol. 203, No. 1-2, pp. 1-60, (Aug. 1, 2000).

* cited by examiner

*Primary Examiner* — Laura B Goddard
(74) *Attorney, Agent, or Firm* — Marianne Fuierer; Olive Law Group, PLLC

(57) ABSTRACT

A stable pharmaceutical formulation comprising a protein of interest, sorbitol and polyethylene glycol (PEG). The sorbitol and protein is present in a molar ratio of 550 to 700 mole of sorbitol:1 mole of protein and the PEG to protein is present in the molar ratio of 2-50:1. The formulation optionally comprising buffer. The formulation in lyophilised form is stable for at least 4 years at 2-8° C. Also provided is a process for preparing the composition and a pharmaceutical kit comprising the same.

17 Claims, 6 Drawing Sheets

Specification includes a Sequence Listing.

SEQUENCE LISTING

<160> NUMBER OF SEQ ID NOS: 10

<210> SEQ ID NO 1
<211> LENGTH: 451
<212> TYPE: PRT
<213> ORGANISM: artificial

<220> FEATURE:
<223> OTHER INFORMATION: Trastuzumab heavy chain

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 214
<212> TYPE: PRT
<213> ORGANISM: artificial
<220> FEATURE:
<223> OTHER INFORMATION: Trastuzumab light chain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 120
<212> TYPE: PRT
<213> ORGANISM: artificial
<220> FEATURE:
<223> OTHER INFORMATION: Trastuzumab VH

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
```

```
                    20                  25                  30
Tyr Ile His Trp Val Arg Gln Ala Pro Gly Lys Gly Leu Glu Trp Val
            35                  40                  45
Ala Arg Ile Tyr Pro Thr Asn Gly Tyr Thr Arg Tyr Ala Asp Ser Val
     50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
            100                 105                 110
Gly Thr Leu Val Thr Val Ser Ser
            115                 120

<210> SEQ ID NO 4
<211> LENGTH: 110
<212> TYPE: PRT
<213> ORGANISM: artificial
<220> FEATURE:
<223> OTHER INFORMATION: Trastuzumab VL

<400> SEQUENCE: 4

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Val Asn Thr Ala
                    20                  25                  30
Val Ala Trp Tyr Gln Gln Lys Pro Gly Lys Ala Pro Lys Leu Leu Ile
            35                  40                  45
Tyr Ser Ala Ser Phe Leu Tyr Ser Gly Val Pro Ser Arg Phe Ser Gly
     50                  55                  60
Ser Arg Ser Gly Thr Asp Phe Thr Leu Thr Ile Ser Ser Leu Gln Pro
 65                  70                  75                  80
Glu Asp Phe Ala Thr Tyr Tyr Cys Gln Gln His Tyr Thr Thr Pro Pro
                 85                  90                  95
Thr Phe Gly Gln Gly Thr Lys Val Glu Ile Lys Arg Thr Val
            100                 105                 110

<210> SEQ ID NO 5
<211> LENGTH: 10
<212> TYPE: PRT
<213> ORGANISM: artificial
<220> FEATURE:
<223> OTHER INFORMATION: Trastuzumab HCDR1

<400> SEQUENCE: 5

Gly Phe Asn Ile Lys Asp Thr Tyr Ile His
 1               5                  10

<210> SEQ ID NO 6
<211> LENGTH: 17
<212> TYPE: PRT
<213> ORGANISM: artificial
<220> FEATURE:
<223> OTHER INFORMATION: Trastuzumab HCDR2

<400> SEQUENCE: 6

Arg Ile Tyr Pro Thr Asn Gly Tyr Thr Arg Tyr Ala Asp Ser Val Lys
 1               5                  10                  15
Gly
```

```
<210> SEQ ID NO 7
<211> LENGTH: 11
<212> TYPE: PRT
<213> ORGANISM: artificial
<220> FEATURE:
<223> OTHER INFORMATION: Trastuzumab HCDR3

<400> SEQUENCE: 7

Trp Gly Gly Asp Gly Phe Tyr Ala Met Asp Tyr
1               5                   10

<210> SEQ ID NO 8
<211> LENGTH: 11
<212> TYPE: PRT
<213> ORGANISM: artificial
<220> FEATURE:
<223> OTHER INFORMATION: Trastuzumab LCDR1

<400> SEQUENCE: 8

Arg Ala Ser Gln Asp Val Asn Thr Ala Val Ala
1               5                   10

<210> SEQ ID NO 9
<211> LENGTH: 7
<212> TYPE: PRT
<213> ORGANISM: artificial
<220> FEATURE:
<223> OTHER INFORMATION: Trastuzumab LCDR2

<400> SEQUENCE: 9

Ser Ala Ser Phe Leu Tyr Ser
1               5

<210> SEQ ID NO 10
<211> LENGTH: 9
<212> TYPE: PRT
<213> ORGANISM: Artificial
<220> FEATURE:
<223> OTHER INFORMATION: Trastuzumab LCDR3

<400> SEQUENCE: 10

Gln Gln His Tyr Thr Thr Pro Pro Thr
1               5
```

STABLE PROTEIN FORMULATIONS COMPRISING A MOLAR EXCESS OF SORBITOL

CROSS-REFERENCE TO RELATED APPLICATIONS

The present application is the U.S. national phase application filed under 35 U.S.C. § 371 claiming benefit to International Patent Application No. PCT/IB2015/052789, filed on Apr. 16, 2015, which is entitled to priority to provisional Indian patent application 1989/CHE/2014 filed on Apr. 16, 2014 with the Indian Patent Office, each of which applications are hereby incorporated herein by reference in their entireties.

REFERENCE TO A SEQUENCE LISTING SUBMITTED AS A TEXT FILE VIA EFS-WEB

The sequence listing of the sequences mentioned herein is submitted electronically as a ST25.txt formatted sequence listing with a file named CM470248.5T25.TXT.

FIELD OF THE INVENTION

The subject matter herein is directed to protein formulations suitable for administration to a subject, wherein the formulations are stable and comprise a specified molar excess of sorbitol and polyethylene glycol in defined amount. Process of preparation of the composition and pharmaceutical kit are also included in the purview of the present invention

BACKGROUND

Proteins are complex molecules with defined primary, secondary, tertiary and in some cases quaternary structures, all of which play a role in imparting specific biological function. A variety of proteins, in particular antibodies, are available for pharmaceutical applications. However, these large, complex molecules are more difficult to formulate for administration to a subject than traditional organic and inorganic drugs. Structural complexity of biological pharmaceuticals, such as proteins renders them susceptible to various processes that result in structural and functional instability as well as loss of safety. For a protein to remain biologically active, a formulation must preserve the conformational integrity of at least a core sequence of the protein's amino acids while at the same time protecting the protein's multiple functional groups from degradation. With respect to these instability processes or degradation pathways, a protein can undergo a variety of covalent and non-covalent reactions or modifications in solution.

Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from deamidation, racemization, hydrolysis, oxidation, beta elimination or disulfide exchange. Physical instability can result from denaturation, aggregation, precipitation or adsorption, for example. The three most common protein degradation pathways are protein aggregation, deamidation and oxidation.

Protein drugs are susceptible to the physical degradation process of irreversible aggregation. Protein aggregation is of particular interest in polypeptide production because it often results in diminished bioactivity that affects drug potency, and also can elicit serious immunological or antigenic reactions in patients. Chemical degradation of a protein therapeutic, including degradation of the chemical structure by, for example, chemical modification, also has been implicated in increasing its immunogenic potential.

Long-term stability of a therapeutic protein is a particularly beneficial criterion for safe, consistent and efficacious treatments. Loss of functionality of the therapeutic within a preparation will decrease its effective concentration for a given administration. Similarly, undesired modifications of a therapeutic can affect the activity and/or the safety of a preparation, leading to loss of efficacy and risk of adverse side effects. Thus, stable protein formulations require that both physical and chemical degradation pathways of the drug be minimized.

Many protein preparations intended for human use require stabilizers to prevent denaturation, aggregation and other alterations to the proteins prior to the use of the preparation. This instability is manifested in the formation of soluble/insoluble particles, and is often increased when the protein preparation is stored over time and during shipping. A major aim in the development of protein drug formulations is to maintain both protein solubility, stability and bioactivity.

However, the use of excipients for one purpose such as stabilization can often lead to other unforeseen problems with compatibility of other components and the manufacture of the formulation. The following disclosure addresses this shortcoming of the art.

SUMMARY OF THE INVENTION

The presently disclosed subject matter is directed to a stable formulation comprising a protein, a specified molar excess of sorbitol, and polyethylene glycol (PEG), methods of preparing the formulation and methods of administering the formulation to subjects in need thereof. In some embodiments, the protein present in the formulation is an antibody, such as an antibody that specifically binds HER2. In some of these embodiments, the anti-HER2 antibody is trastuzumab.

In some embodiments, the subject matter described herein is directed to a stable formulation comprising: a protein (e.g., antibody); sorbitol and polyethylene glycol (PEG), wherein sorbitol and protein are present in a molar ratio of 550 to 750 mole of sorbitol to about 1 mole of protein (e.g., antibody).

In other embodiments, the subject matter described herein is directed to a stable reconstituted formulation comprising a protein (e.g., antibody) in an amount of from about 5 mg/mL to about 50 mg/mL and a diluent, wherein the reconstituted formulation has been prepared from a lyophilized mixture comprising a protein (e.g., antibody); sorbitol and polyethylene glycol (PEG), wherein in the lyophilized mixture, the sorbitol is present in a molar ratio of about 550 to about 750 mole of sorbitol:1 mole of protein (e.g., antibody) and the mole ratio of PEG to protein (e.g., antibody) is in a range of about 2:1 to 50:1.

In another embodiment, the subject matter disclosed herein is directed to an article of manufacture or pharmaceutical kit which comprises: (a) a container which holds a lyophilized mixture comprising the protein (e.g., antibody); sorbitol present in a molar ratio of about 550 to about 750 mole of sorbitol:1 mole of protein (e.g., antibody); and polyethylene glycol (PEG) present in a PEG to protein (e.g., antibody) molar ratio range of about 2:1 to 50:1; and (b) instructions for reconstituting the lyophilized mixture with a diluent. The article of manufacture or pharmaceutical kit may further comprise a second container which holds a diluent (e.g. bacteriostatic water for injection (BWFI)).

In another embodiment, the subject matter disclosed herein is also directed to methods of administering therapeutically effective amounts of the formulations to a subject for the treatment of a disease or disorder.

In another embodiment, the subject matter disclosed herein is directed to methods of preparing the lyophilized and liquid formulations described herein.

BRIEF DESCRIPTION OF THE ACCOMPANYING DRAWINGS

FIG. 1 depicts a flowchart for one embodiment of the preparation methods for a pharmaceutical formulation described herein.

FIG. 2 is a representative SEC chromatogram of test formulation 6 as described herein. The monomer fraction elutes at 28.54 min and the aggregate elutes at 24.42 minutes. An increase in the aggregate is seen in sample stored at 40° C. for 3 weeks (red trace) when compared to the sample at initial condition (blue trace).

FIG. 3 is a representative IEX chromatogram of test formulation 6 as described herein. The zero variant main peak elutes between 32-33 mins, the acidic and basic variants are composed of multiple charged species that elute starting at 20 minutes and 34 minutes, respectively. The chromatograms have been normalized with respect to the main peak. An increase in the acidic and basic variants are seen in sample stored at 40° C. for 3 weeks (upper chromatogram) when compared to the sample at initial condition (lower chromatogram).

DETAILED DESCRIPTION OF THE INVENTION

Figure 1:
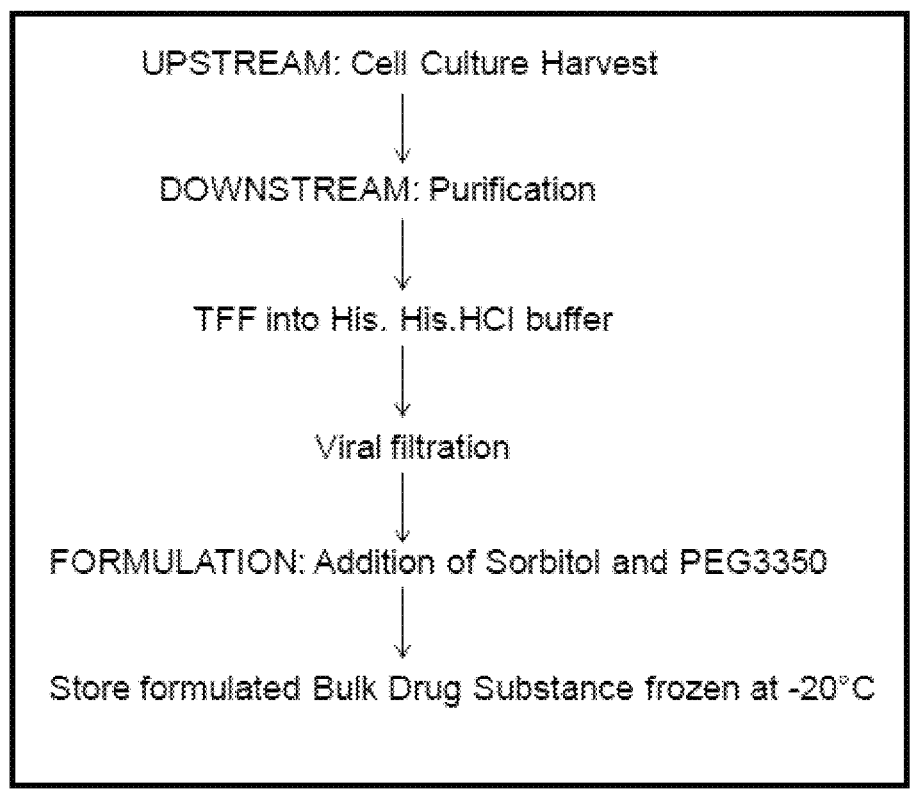

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims.

I. Pharmaceutical Formulations

The stable formulations described herein contain a protein (e.g., an antibody) and a specified molar excess of sorbitol along with polyethylene glycol (PEG).

Proteins

As used herein, the terms "protein" and "polypeptide" are used interchangeably and are intended to encompass a singular "polypeptide" as well as plural "polypeptides," and refers to a molecule composed of monomers (amino acids) linearly linked by amide bonds (also known as peptide bonds). The terms "protein" and "polypeptide" refer to any chain or chains of two or more amino acids, and do not refer to a specific length of the product. Thus, peptides, dipeptides, tripeptides, oligopeptides, amino acid chain, or any other term used to refer to a chain or chains of two or more amino acids, are included within the definition of "protein." The terms "protein" and "polypeptide" are also intended to refer to the products of post-translational modifications of the protein, including without limitation glycosylation, acetylation, phosphorylation, amidation, derivatization by known protecting/blocking groups, and proteolytic cleavage. A polypeptide may be derived from a natural biological source or produced by recombinant technology, but is not necessarily translated from a designated nucleic acid sequence. It may be generated in any manner, including by chemical synthesis. A protein may comprise naturally occurring amino acids or one or more non-classical amino acids.

A polypeptide may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure.

In some embodiments, the protein is unstable. For example, the protein is prone to aggregation, deamidation (e.g. Asn deamidation), oxidation (e.g. Met oxidation), isomerization (e.g. Asp isomeriation). In some embodiments, the protein is prone to deamidation.

A non-limiting example of a protein that can be formulated as described herein is an antibody. In some of these embodiments, the antibody is a full-length antibody. In certain embodiments, the antibody is a monoclonal antibody. The monoclonal antibody can be human, humanized or chimeric. In some of these embodiments, the monoclonal antibody is an IgG1 antibody.

The terms "antibody" and "immunoglobulin" are used interchangeably herein and refer to various broad classes of polypeptides that can be distinguished biochemically. The general structure of antibodies is well known to those of skill in the art. See, e.g., Harlow et al. (1988) *Antibodies: A Laboratory Manual* (2nd ed.; Cold Spring Harbor Laboratory Press). The terms "antibody" and "antibodies" broadly encompass naturally occurring forms of antibodies and recombinant antibodies such as single-chain antibodies, chimeric and humanized antibodies and multispecific antibodies as well as fragments and derivatives of all of the foregoing, which fragments and derivatives have at least an antigenic binding site. Antibody derivatives may comprise a protein or chemical moiety conjugated to the antibody. The term "antibody" is used in the broadest sense and covers fully assembled antibodies (e.g., polyclonal, monoclonal, multispecific, human, humanized, primatized, chimeric antibodies), antibody fragments that can bind antigen (e.g., Fab', F(ab')$_2$, Fv, single chain antibodies, diabodies), and recombinant peptides comprising the foregoing.

In some embodiments, the antibodies contained in the formulations described herein are monoclonal antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts. The term is not limited regarding the species or source of the antibody. The term encompasses whole immunoglobulins as well as fragments such as Fab, F(ab')2, Fv, and others which retain the antigen binding function of the antibody. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see, e.g., U.S. Pat. No. 4,816,567). The "monoclonal antibodies" may also be isolated from phage antibody libraries using the techniques described in, for example, Clackson et al. (1991) Nature 352:624-628; Marks et al. (1991) J. Mol. Biol. 222:581-597; and U.S. Pat. No. 5,514,548.

In certain embodiments, the antibody of the presently disclosed formulation is a chimeric antibody. As used herein, the term "chimeric antibody" refers to any antibody wherein the immunoreactive region or site is obtained or derived from a first species and the constant region (which may be intact, partial or modified in accordance with the instant invention) is obtained from a second species. In some embodiments, the target binding region or site will be from a non-human source (e.g., mouse or primate) and the constant region is human.

In some of those embodiments wherein the antibody of the presently disclosed formulation is a chimeric antibody, the chimeric antibody is a humanized antibody. A "humanized antibody" is a specific type of chimeric antibody which comprises one or more framework regions having substantially the amino acid sequence of a human immunoglobulin and one or more CDRs having substantially the amino acid sequence of a non-human immunoglobulin. For example, as described elsewhere herein, the anti-HER2 antibody trastuzumab is a humanized version of the murine 4D5 antibody.

The FRs and CDRs of a humanized antibody need not correspond precisely to the parental sequences. For example, one or more residues in the donor CDR or the consensus or germline framework sequence may be altered (e.g., mutagenized) by substitution, insertion or deletion such that the resulting amino acid residue is no longer identical to the original residue in the corresponding position in either parental sequence but the antibody nevertheless retains the function of binding to its antigen. Such alteration typically will not be extensive and will be conservative alterations. Usually, at least 75% of the humanized antibody residues will correspond to those of the parental consensus or germline framework and donor CDR sequences, more often at least 90%, and most frequently greater than 95%, or greater than 98% or greater than 99%.

In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

In other embodiments, the presently disclosed formulations comprise a human antibody. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

Antibodies of the presently disclosed formulations may be "multispecific," e.g., bispecific, trispecific, or of greater multispecificity, meaning that it recognizes and binds to two or more different epitopes present on one or more different antigens (e.g., proteins) at the same time. Thus, whether an antibody is "monospecific" or "multispecific," e.g., "bispecific," refers to the number of different epitopes with which a binding polypeptide reacts. Multispecific antibodies may be specific for different epitopes of a target polypeptide or may be specific for a target polypeptide as well as for a heterologous epitope, such as a heterologous polypeptide or solid support material.

As used herein the term "valency" refers to the number of potential binding domains, e.g., antigen binding domains, present in an antibody. Each binding domain specifically binds one epitope. When an antibody comprises more than one binding domain, each binding domain may specifically bind the same epitope. An antibody with two binding domains that specifically binds the same epitope is termed "bivalent monospecific," whereas an antibody with two binding domains that bind different epitopes is termed "bivalent bispecific." Antibodies of the presently disclosed formulations may also be bispecific and bivalent for each specificity (termed "bispecific tetravalent antibodies").

Bispecific bivalent antibodies, and methods of making them, are described, for instance in U.S. Pat. Nos. 5,731,168; 5,807,706; 5,821,333; and U.S. Patent Appl. Publ. Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al. (1991) J. Immunol. 147:60-69; U.S. Pat. Nos. 4,474,893; 4,714,681; 4,925,648; 5,573,920; 5,601,819; Kostelny et al. (1992) J. Immunol. 148:1547-1553.

In some embodiments, the antibody is a native antibody. "Native antibodies" and "native immunoglobulins," also referred to herein as "full-length antibodies" are usually heterotetrameric glycoproteins of about 150,000 daltons, composed of two identical light (L) chains and two identical heavy (H) chains. Each light chain is covalently linked to a heavy chain by one disulfide bond to form a heterodimer, and the heterotrameric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. The disulfide bonds typically join the four chains into a "Y" configuration, with the light chains bracketing the heavy chains starting at the mouth of the "Y" and continuing through the variable region. In the heavy chain, the amino acid sequences run from an N-terminus at the forked ends of the Y configuration to the C-terminus at the bottom of each chain.

Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity determining regions (CDRs) or hypervariable regions both in the light chain and the heavy-chain variable domains. The more highly conserved portions of variable domains are called the framework (FR) regions. The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

In certain embodiments, the protein within the presently disclosed formulations is an antibody fragment. For example, fragments of monoclonal antibodies can be formulated into pharmaceutical compositions disclosed herein, wherein the fragments retain some or all of the desired function of the full-length antibody. Such fragments are characterized by properties similar to the corresponding full-length antibody.

"Antibody fragments" comprise a portion of an intact antibody, which in some embodiments, is the antigen-binding or variable region of the intact antibody. Examples of antibody fragments include Fab, Fab', F(ab')$_2$, and Fv fragments; diabodies; linear antibodies (Zapata et al. (1995) Protein Eng. 8(10):1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment of antibodies yields an F(ab')2 fragment that has two antigen-combining sites and is still capable of cross-linking antigen.

Suitable antigen-binding fragments of an antibody for use in the presently disclosed compositions and methods comprise a portion of a full-length antibody, generally the antigen-binding or variable region thereof. Examples of antibody fragments include, but are not limited to, Fab, F(ab')$_2$, and Fv fragments and single-chain antibody molecules. By "Fab" is intended a monovalent antigen-binding fragment of an immunoglobulin that is composed of the light chain and part of the heavy chain. By "F(ab')$_2$" is intended a bivalent antigen-binding fragment of an immunoglobulin that contains both light chains and part of both heavy chains. By "single-chain Fv" or "sFv" or "scFv" antibody fragments is intended fragments comprising the $V_H$ and $V_L$ domains of an antibody, wherein these domains are present in a single polypeptide chain. See, for example, U.S. Pat. Nos. 4,946,778, 5,260,203, 5,455,030, and 5,856,456, herein incorporated by reference. Generally, the Fv polypeptide further comprises a polypeptide linker between the $V_H$ and $V_L$ domains that enables the sFv to form the desired structure for antigen binding. For a review of sFv see Pluckthun (1994) in The Pharmacology of Monoclonal Antibodies, Vol. 113, ed. Rosenburg and Moore (Springer-Verlag, New York), pp. 269-315.

"Fv" is the minimum antibody fragment that contains a complete antigen recognition and binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them.

Various techniques have been developed for the production of antibody fragments. Traditionally, these fragments were derived via proteolytic digestion of intact antibodies (see, e.g., Morimoto et al. (1992) Journal of Biochemical and Biophysical Methods 24:107-117 (1992) and Brennan et al. (1985) Science 229:81). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al. (1992) Bio/Technology 10:163-167). According to another approach, F(ab')$_2$ fragments can be isolated directly from recombinant host cell culture. Other techniques for the production of antibody fragments will be apparent to the skilled practitioner.

In some embodiments, the antibody of the presently disclosed formulations specifically or preferentially binds an epitope.

By "epitope" is intended the part of an antigenic molecule to which an antibody is produced and to which the antibody will bind. Epitopes can comprise linear amino acid residues (i.e., residues within the epitope are arranged sequentially one after another in a linear fashion), nonlinear amino acid residues (referred to herein as "nonlinear epitopes" or "conformational epitopes"; these epitopes are not arranged sequentially), or both linear and nonlinear amino acid residues. Nonlinear epitopes or conformational epitopes can also include amino acid residues that contribute to the overall conformation of the recognition structure of the antibody, but do not necessarily bind the antibody. Typically, epitopes are short amino acid sequences, e.g. about five amino acids in length.

Systematic techniques for identifying epitopes are known in the art and are described, for example, in U.S. Pat. No. 4,708,871, herein incorporated by reference in its entirety. Briefly, in one method, a set of overlapping oligopeptides derived from the antigen may be synthesized and bound to a solid phase array of pins, with a unique oligopeptide on each pin. The array of pins may comprise a 96-well microtiter plate, permitting one to assay all 96 oligopeptides simultaneously, e.g., for binding to a biomarker-specific monoclonal antibody. Alternatively, phage display peptide library kits (New England BioLabs) are currently commercially available for epitope mapping. Using these methods, the binding affinity for every possible subset of consecutive amino acids may be determined in order to identify the epitope that a given antibody binds. Epitopes may also be identified by inference when epitope length peptide sequences are used to immunize animals from which antibodies are obtained. Conformational epitopes may be identified using peptide walking techniques and synthetic peptides (see, for example, Liang et al. (2005) Clinical Chemistry 51:1382-1396; Cochran et al. (2004) J. Immunol. Meth. 287:147-158; Teeling et al. (2006) J. Immunol. 177: 362-371; Timmerman et al. (2004) Molecular Diversity 8:61-77; Lekcharoensuk et al. (2004) J. Virology 78:8135-8145; and Casadio et al. (2007) BMC Bioinformatics (Supp. 1):S1-6; each of which is herein incorporated by reference in its entirety).

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

In certain embodiments of the presently disclosed compositions and methods, the antibody is one that competitively inhibits the binding of a reference antibody (e.g., trastuzumab) to an epitope on the target antigen. An antibody is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody (e.g., trastuzumab) to a given epitope by at least 90%, at least 80%, at least 70%, at least 60%, or at least 50%.

In some of the embodiments wherein the protein within the presently disclosed formulations is an antibody, the antibody binds to its target antigen with relatively high affinity. As used herein, the term "affinity" refers to a measure of the strength of the binding of an individual epitope with the CDR of an immunoglobulin molecule. See, e.g., Harlow et al. (1988) *Antibodies: A Laboratory Manual* (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Antibodies of the presently disclosed compositions and methods exhibit little to no cross-reactivity to other related epitopes.

As a non-limiting example, in those embodiments wherein the antibody within the formulation is an anti-HER2 antibody, the anti-HER2 antibody displays little to no cross-reactivity with other HER family members (e.g., EGFR/HER1, HER3, and HER4). As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein)

to a reference epitope. An antibody may be deemed "highly specific" for a certain epitope, if it does not bind any other analog, ortholog, or homolog of that epitope.

In certain embodiments, the antibody of the presently disclosed formulations is one that targets and antagonizes a protein that contributes to the development and/or maintenance of a disease state. In some of these embodiments, the disease is cancer and the antibody targets a protein encoded by an oncogene. As used herein, the term "oncogene" refers to a gene that encodes a gene product (e.g., a protein) that contributes to the development and/or maintenance of cancer or a transformed phenotype. In some of those embodiments wherein the antibody within the formulation targets a protein encoded by an oncogene, the target protein is a growth factor receptor tyrosine kinase.

The HER family of receptor tyrosine kinases are important mediators of cell growth, differentiation and survival. Loss of the regulation of growth factor RTK activation often results in abnormal cellular proliferation and tumorigenesis. The receptor family includes four distinct members including epidermal growth factor receptor (EGFR, ErbB1, or HER1), HER2 (ErbB2, Neu, or p185$^{neu}$), HER3 (ErbB3) and HER4 (ErbB4 or tyro2).

In certain embodiments, the protein of the presently disclosed formulations is an anti-HER2 antibody. The sequence of the erb-b2 gene that encodes HER2 is known in the art and found on band q21 of chromosome 17. Sequences of the HER2 protein are also known in the art and include, but are not limited to Genbank Accession Nos. NP_001005862, NP_004439, AAA75493 or AAA35978, each of which is herein incorporated by reference. The HER2 protein has an extracellular domain, a transmembrane domain that includes two cysteine-rich repeat clusters, and an intracellular kinase domain with autophosphorylation sites. In reference to the 1255 amino acid human HER2 isoform 1, which is set forth in SEQ ID NO: 11, the extracellular domain is from amino acid residues 23-652, the transmembrane domain spans residues 653-675, and residues 676-1255 make up the cytoplasmic domain. Generally, the anti-HER2 antibody targets the extracellular domain of HER2.

In certain embodiments, the protein of the presently disclosed formulations is the monoclonal antibody trastuzumab (Herceptin®) (U.S. Pat. No. 5,821,337, which is herein incorporated by reference in its entirety) or an active variant thereof capable of binding and antagonizing HER2. Trastuzumab is a humanized IgG1 kappa light chain monoclonal antibody that selectively binds to HER-2. Trastuzumab prevents dimerization of the receptor essential for intracellular signaling, leading to inhibition of cell proliferation. This results in an inhibition of tumor growth and metastasis. In addition, antibody dependent cell mediated toxicity as well as HER2 internalization and degradation also occurs in vivo, thereby further reducing the proliferation potential of tumor cells. Trastuzumab is approved for intravenous use in combination with multiple chemotherapeutic agents in adjuvant treatment of HER2 over-expressing breast cancer and metastatic HER2 over-expressing breast cancer as well as HER2 over-expressing metastatic cancer of the stomach and gastroesophageal junction. Reference to trastuzumab shall be understood to include a biosimilar form of trastuzumab. Reference to trastuzumab shall be understood to include an antibody comprising or consisting of the heavy chain amino acid sequence and light chain amino acid sequence of trastuzumab or an active variant thereof.

Thus, in some of those embodiments wherein the protein of the presently disclosed formulations comprises an anti-HER2 antibody, the antibody comprises a heavy chain having the sequence set forth in SEQ ID NO: 1 and a light chain having the sequence set forth in SEQ ID NO: 2 or active variant thereof. One of skill in the art will recognize that the constant region of the heavy chain of trastuzumab comprises the G1m-1(17) allele with lysine at position 217 of SEQ ID NO: 1 and the constant region of the light chain comprises the Km-3 allele with alanine at position 153 and a valine at position 191 of SEQ ID NO: 2 or active variant thereof. In certain embodiments, an active variant of trastuzumab is comprised within the presently disclosed formulations. As used herein, an "active variant" in reference to trastuzumab is a full-length antibody or an antigen-binding fragment thereof that comprises at least one of the CDRs of trastuzumab and is capable of binding to HER2 and antagonizing its activity, which can result in any one or more of the following events: preventing dimerization of the receptor, inhibition of cell proliferation, inhibition of tumor growth, inhibition of tumor metastasis, antibody dependent cell mediated toxicity, HER2 internalization, HER2 degradation, reducing the proliferation potential of tumor cells, apoptosis of HER2-overexpressing tumor cell.

Thus, in some embodiments, the presently disclosed formulations comprise an active variant of trastuzumab that competitively inhibits binding of trastuzumab to HER2.

In other embodiments, the anti-HER2 antibody is one that binds to the same or similar epitope as trastuzumab. See Cho et al. (2003) Nature 421(6924):756-760, which is incorporated by reference in its entirety.

In other embodiments, the anti-HER2 antibody comprises a heavy chain having the sequence set forth in SEQ ID NO: 1.

In other embodiments, the anti-HER2 antibody comprises a light chain having the sequence set forth in SEQ ID NO: 2.

In other embodiments, the anti-HER2 antibody comprises a variable heavy ($V_H$) domain having the sequence set forth in SEQ ID NO: 3.

In yet other embodiments, the anti-HER2 antibody comprises a variable light ($V_L$) domain having the sequence set forth in SEQ ID NO: 4.

In some of these embodiments, the anti-HER2 antibody suitable for formulation as described herein comprises a $V_H$ domain having the sequence set forth in SEQ ID NO: 3 and a $V_L$ domain having the sequence set forth in SEQ ID NO: 4.

In certain embodiments, the anti-HER2 antibody of the formulation comprises at least one CDR of trastuzumab. Thus, the anti-HER2 antibody may comprise at least one of the CDRs set forth in SEQ ID NO: 5, 6, 7, 8, 9, and 10 (CDR1, CDR2, CDR3 of the $V_H$ domain of trastuzumab, and CDR1, CDR2, and CDR3 of the $V_L$ domain of trastuzumab, respectively). In some of these embodiments, the anti-HER2 antibody comprises a $V_H$ CDR1 having the sequence set forth in SEQ ID NO: 5, a $V_H$ CDR2 having the sequence set forth in SEQ ID NO: 6, a $V_H$ CDR3 having the sequence set forth in SEQ ID NO: 7, a $V_L$ CDR1 having the sequence set forth in SEQ ID NO: 8, a $V_L$ CDR2 having the sequence set forth in SEQ ID NO: 9, and a $V_L$ CDR3 having the sequence set forth in SEQ ID NO: 10.

While a widely recognized HER2 antibody is trastuzumab, the presently disclosed methods and compositions are not limited to the use of this antibody, however the presently disclosed methods and compositions are particularly suited to this antibody. Other HER2 antibodies are also suitable for use in the presently disclosed methods and compositions. Examples of other such HER2 antibodies include, but are not limited to, the 4D5 antibody (described in U.S. Pat. Nos. 5,677,171 and 5,772,997); and the 520C9 antibody and its functional equivalents, designated 452F2, 736G9, 741F8, 758G5, and 761B10 (described in U.S. Pat. No. 6,054,561); rhuMAb 2C4 or pertuzumab (Perjeta®) (described in U.S. Pat. No. 8,372,396); herein incorporated by reference. Other HER2 antibodies with various properties have been described in Tagliabue et al. Int. J. Cancer 47:933-937 (1991); McKenzie et al. Oncogene 4:543-548 (1989); Maier et al. Cancer Res. 51:5361-5369 (1991); Bacus et al. Molecular Carcinogenesis 3:350-362 (1990); Stancovski et al. PNAS (USA) 88:8691-8695 (1991); Bacus et al. Cancer Research 52:2580-2589 (1992); Xu et al. Int. J. Cancer 53:401-408 (1993); WO94/00136; Kasprzyk et al. Cancer Research 52:2771-2776 (1992); Hancock et al. Cancer Res. 51:4575-4580 (1991); Shawver et al. Cancer Res. 54:1367-1373 (1994); Arteaga et al. Cancer Res. 54:3758-3765 (1994); Harwerth et al. J. Biol. Chem. 267:15160-15167 (1992); U.S. Pat. No. 5,783,186; and Klapper et al. Oncogene 14:2099-2109 (1997); each of which is herein incorporated by reference in its entirety. In addition, new HER2 antibodies can be generated using methods known in the art, or those described here.

In certain embodiments, the presently disclosed formulations comprise more than one type of protein (e.g., antibody). For example, it has been observed that with extracellularly expressed antigens such as HER2, administration of two different anti-HER2 antibodies directed to different epitopes of the protein resulted in anti-tumor activity in vivo and in vitro. Spiridon et al, Clin. Cancer Res. 8: 1720-30 (2002) (incorporated by reference herein in its entirety). Indeed, synergistic effects have been demonstrated for administration of two different anti-HER2 antibodies (Spiridon, 2002; Friedman et al. Proc. Natl. Acad. Sci USA 702: 1915-1920 (2005)); and a combination of one anti-HER2 and one anti-EGFR antibody (Larbouret et al., Clin. Cancer Res. 75:3356-3362 (2007)). These synergistic effects are the result of hypercrosslinking of the cell surface molecules by mixing high affinity antibodies directed against different epitopes on the same molecule (Spiridon, 2002). Simultaneous engagement of more than one epitope causes large aggregates of antibody-receptor complexes to form. These large aggregates are endocytosed faster than smaller antibody complexes which results in accelerated clearance of the receptors (Friedman, 2005). In a non-limiting example, the presently disclosed formulation comprises trastuzumab or an active variant thereof and pertuzumab or an active variant thereof.

Sorbitol

As used herein, "sorbitol" refers to a polyhydric alcohol having a molecular formula of $C_6H_{14}O_6$ and a molecular weight of 182.2. It is also known as D-glucitol. It has the following chemical structure:

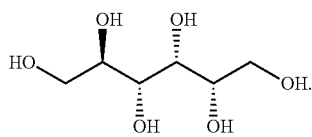

Sorbitol belongs to the category of excipients and additives referred to as Generally Regarded As Safe (GRAS).

In an embodiment, the subject matter described herein is directed to a pharmaceutical formulation comprising a protein (e.g., an antibody) and sorbitol, wherein the molar ratio of said sorbitol to said protein (e.g., antibody) is about 550 to about 700 mole sorbitol:about 1 mole protein (e.g., antibody). In certain embodiments, the molar ratios are from about 600 to about 660 mole sorbitol:about 1 mole protein (e.g., antibody). In some of these embodiments, the molar ratios are from about 615 to about 655 mole sorbitol:about 1 mole protein (e.g., antibody). In other embodiments, the molar ratios are from about 620 to about 640 mole sorbitol:about 1 mole protein (e.g., antibody). In yet other embodiments, the molar ratio is about 631 mole sorbitol:about 1 mole protein (e.g., antibody). In some embodiments, the sorbitol is present at a concentration of about 90 mM to about 120 mM. In embodiments, the sorbitol is present at a concentration of about 100 mM to about 110 mM. In certain embodiments, the concentration of sorbitol is about 105.4 mM.

In an embodiment, the subject matter described herein is directed to a pharmaceutical formulation comprising an anti-HER2 antibody (e.g., trastuzumab as discussed herein) and sorbitol, wherein the molar ratio of said sorbitol to said antibody is about 550 to about 700 mole sorbitol:about 1 mole antibody. In certain embodiments, the molar ratios are from about 600 to about 660 mole sorbitol:about 1 mole antibody. In some of these embodiments, the molar ratios are from about 615 to about 655 mole sorbitol:about 1 mole antibody. In other embodiments, the molar ratios are from about 620 to about 640 mole sorbitol:about 1 mole antibody. In yet other embodiments, the molar ratio is about 631 mole sorbitol:about 1 mole antibody. In some embodiments, the sorbitol is present at a concentration of about 90 mM to about 120 mM. In embodiments, the sorbitol is present at a concentration of about 100 mM to about 110 mM. In certain embodiments, the concentration of sorbitol is about 105.4 mM.

In an embodiment, the subject matter described herein is directed to a pharmaceutical formulation comprising trastuzumab and sorbitol, wherein the molar ratio of said sorbitol to said trastuzumab is about 550 to about 700 mole sorbitol:about 1 mole trastuzumab. In certain embodiments, the molar ratios are from about 600 to about 660 mole sorbitol:about 1 mole trastuzumab. In some of these embodiments, the molar ratios are from about 615 to about 655 mole sorbitol:about 1 mole trastuzumab. In other embodiments, the molar ratios are from about 620 to about 640 mole sorbitol:about 1 mole trastuzumab. In yet other embodiments, the molar ratio is about 631 mole sorbitol:about 1 mole trastuzumab. In some embodiments, the sorbitol is present at a concentration of about 90 mM to about 120 mM. In embodiments, the sorbitol is present at a concentration of about 100 mM to about 110 mM. In certain embodiments, the concentration of sorbitol is about 105.4 mM.

In an embodiment, the subject matter described herein is directed to a pharmaceutical formulation comprising trastuzumab and sorbitol, wherein the molar ratio of said sorbitol to said trastuzumab is about 631 mole sorbitol:about 1 mole trastuzumab.

In an embodiment, the subject matter described herein is directed to a pharmaceutical formulation comprising trastuzumab and about about 100 mM to about 110 mM sorbitol.

In an embodiment, the subject matter described herein is directed to a pharmaceutical formulation comprising trastuzumab and about 105.4 mM sorbitol.

Polyethylene Glycol (PEG)

As used herein, "polyethylene glycol" refers to a compound composed of repeating ethylene glycol units: H—(O—CH2-CH2)n-OH; wherein n=average number of oxyethylene groups.

Purified PEG is most commonly available commercially as mixtures of different oligomer sizes in broadly or narrowly defined molecular weight (MW) ranges. For example, "PEG 3350" typically denotes a preparation that includes a mixture of PEG molecules having an average MW of 3350 g/mol.

As used herein, PEG refers to as biologically inert, non-immunogenic chemical that confers greater water solubility to proteins.

In an embodiment, the subject matter described herein is directed to a pharmaceutical formulation comprising a protein (e.g., an antibody), sorbitol and polyethylene glycol (PEG), wherein the molar ratio of said sorbitol to said protein (e.g., antibody) is about 550 to about 700 mole sorbitol:1 mole protein (e.g., antibody) and the molar ratio of polyethylene glycol (PEG) to said protein is in a range of about 2:1 to 50:1. It has been determined that the presence of polyethylene glycol in combination with sorbitol in the ratios specified herein provide a formulation having desirable stability. Useful polyethylene glycols include those wherein the molecular weights are from about 2000 g/mol to about 5000 g/mol. In certain embodiments, the polyethylene glycols have a molecular weight from about 3000 g/mol to about 4000 g/mol. In other embodiments, the polyethylene glycol is PEG 3350 which is the most preferred.

Without being bound by any theory or mechanism of action, it is believed that in particular embodiments, sorbitol and the polyethylene glycol can function as lyoprotectants by maintaining the integrity of the lyophilized cake structure even to the point of preventing, inhibiting or minimizing collapse of the lyophilized cake structure.

In specific embodiments, the formulations comprising sorbitol and PEG can further contain excipients but do not contain other lyoprotectants, e.g., trehalose, sucrose and/or mannitol. Thus in a embodiment, the formulations comprise an antibody as described herein, sorbitol in specified ratios and amounts as described herein, and PEG in specified ratios and amounts as described herein with the proviso that the formulations do not contain an additional non-reducing sugar, such as trehalose, sucrose and/or mannitol.

Useful amounts of polyethylene glycol present in the formulation include a mole ratio of at least 2:1, PEG to protein (e.g., antibody). In some embodiments, the amount of polyethylene glycol present in the formulation include a mole ratio of from about 2:1 to about 50:1, PEG to protein (e.g., antibody). In certain embodiments, the polyethylene glycol is present in the formulation in a molar ratio of at from about least 5:1 to about 40:1, PEG to protein (e.g., antibody). In other embodiments, the polyethylene glycol is present in the formulation in a molar ratio of at from about least 5:1 to about 15:1, PEG to protein (e.g., antibody). In yet other embodiment, the polyethylene glycol is present in the formulation in a molar ratio of about 10:1, PEG to protein (e.g., antibody).

In some embodiments, the PEG is present at a concentration of about 1.0 mM to about 2.5 mM. In other embodiments, the PEG is present at a concentration of about 1.5 mM to about 1.9 mM. In certain embodiments, the concentration of PEG is about 1.67 mM.

In certain embodiments, the formulation comprises a protein (e.g., an antibody); sorbitol, wherein the molar ratio of the sorbitol to the protein (e.g., antibody) is about 631 mole sorbitol:about 1 mole protein (e.g., antibody); and PEG 3350, wherein the molar ratio of PEG 3350 to the protein (e.g., antibody) is about 10:1.

In certain embodiments, the formulation comprises an anti-HER2 antibody; sorbitol, wherein the molar ratio of the sorbitol to the antibody is about 631 mole sorbitol:about 1 mole antibody; and PEG 3350, wherein the molar ratio of PEG 3350 to the antibody is about 10:1.

In certain embodiments, the formulation comprises trastuzumab; sorbitol, wherein the molar ratio of the sorbitol to the trastuzumab is about 631 mole sorbitol:about 1 mole trastuzumab; and PEG 3350, wherein the molar ratio of PEG 3350 to the trastuzumab is about 10:1.

Other Excipients

The presently disclosed formulations are suitable for lyophilization. In this aspect, the formulation is a solid and can be in the form of a powder or cake. The lyophilized formulation is stable as described elsewhere herein. However, in some embodiments, the formulation does not necessarily have to be lyophilized and a liquid formulation does not necessarily have to be reconstituted from a lyophilized form. Lyophilization of a protein (e.g., antibody) usually requires a lyoprotectant to be present in a specific and adequate ratio to the protein (e.g., antibody) in order to afford protection during sublimation. A "lyoprotectant" is a molecule which, when combined with a protein of interest, significantly prevents or reduces chemical and/or physical instability of the protein upon lyophilization and subsequent storage. The lyoprotectant is added to the pre-lyophilized formulation such that the protein essentially retains its physical and chemical stability and integrity upon lyophilization and storage. In the art, it is typical that non-reducing sugars are generally used in formulations to avoid undesired Maillard-type reactions that may occur due to reaction between active aldehyde group with the reactive amino acids of the protein backbone. Lyophilized HER2 antibody formulations are described in U.S. Pat. Nos. 6,267,958 and 6,685,940, and International Appl. Publ. No. WO 97/04801, each of which is herein incorporated by reference in its entirety.

In an embodiment, the subject matter described herein is directed to a reconstituted formulation for administration. A "reconstituted" formulation is one which has been prepared by dissolving a lyophilized protein formulation in a diluent such that the protein is dispersed in the reconstituted formulation. The reconstituted formulation is suitable for administration (e.g. parenteral administration) to a subject to be treated with the protein of interest and, in certain embodiments of the invention, may be one which is suitable for subcutaneous administration.

The reconstituted formulation comprises protein (e.g., an antibody); and sorbitol, wherein the molar ratio of said sorbitol to said protein (e.g., antibody) is about 550 to about 700 mole sorbitol:about 1 mole protein (e.g., antibody); and a diluent. A "diluent" refers to a pharmaceutically acceptable (safe and non-toxic for administration to a human) liquid that is useful for the preparation of a reconstituted formulation.

Exemplary diluents include sterile water, bacteriostatic water for injection (BWFI), a pH buffered solution (e.g. phosphate-buffered saline), sterile saline solution, Ringer's solution or dextrose solution. The formulations are generally sterile, and this can be achieved according to the procedures known to the skilled person for generating sterile pharmaceutical formulations suitable for administration to human subjects, including filtration through sterile filtration membranes, prior to, or following, preparation of the formulation.

The diluent can contain preservatives. A "preservative" is a compound which can be added to the diluent to essentially reduce bacterial action in the reconstituted formulation, thus facilitating the production of a multi-use reconstituted formulation, for example. Non-limiting examples of preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride, aromatic alcohols such as phenol, butyl and benzyl alcohol, allyl parabens such as methyl or propyl paraben, catechol, resorcinol, cyclohexanol, 3-pentanol, and m-cresol. In some of those embodiments wherein a preservative is present, the preservative is benzyl alcohol.

In an embodiment, a liquid formulation contains a protein (e.g., an antibody); sorbitol, wherein the molar ratio of sorbitol to protein (e.g., antibody) is about 550 to about 700 mole sorbitol:about 1 mole protein (e.g., antibody); polyethylene glycol (PEG), wherein the molar ratio of PEG to protein (e.g., antibody) is in a range of about 2:1 to 50:1; and a diluent.

In another embodiment, a liquid formulation contains an anti-HER2 antibody; and sorbitol, wherein the molar ratio of sorbitol to antibody is about 550 to about 700 mole sorbitol: about 1 mole antibody; polyethylene glycol (PEG), wherein the molar ratio of PEG to protein (e.g., antibody) is in a range of about 2:1 to 50:1; and a diluent.

In another embodiment, a liquid formulation contains trastuzumab; and sorbitol, wherein the molar ratio of sorbitol to trastuzumab is about 550 to about 700 mole sorbitol: about 1 mole trastuzumab; polyethylene glycol (PEG), wherein the molar ratio of PEG to protein (e.g., antibody) is in a range of about 2:1 to 50:1; and a diluent.

In some liquid formulations, the protein (e.g., antibody) is present at a concentration of about 5 mg/mL to about 50 mg/mL. In some of these embodiments, the protein is present at a concentration of about 10 mg/mL to about 40 mg/mL. In other embodiments, the protein is present at a concentration of about 15 mg/mL to about 35 mg/mL. In certain embodiments, the protein is present at a concentration of about 21 mg/mL.

In some liquid formulations, an anti-HER2 antibody is present at a concentration of about 21 mg/mL.

In some liquid formulations, trastuzumab is present at a concentration of about 21 mg/mL.

Additional useful concentrations of protein also include from about 0.10 mM to about 0.25 mM; from about 0.15 mM to about 0.18 mM; and about 0.167 mM.

The formulations described herein can further comprise excipients. An "excipient" is intended to mean a therapeutically inactive substance. Excipients can be included in a formulation for a wide variety of purposes including, for example, as a diluent, vehicle, buffer, stabilizer, tonicity agent, bulking agent, surfactant, cryoprotectant, lyoprotectant, anti-oxidant, metal ion source, chelating agent and/or preservative. Excipients are well known in the art and can be found described in, for example, Wang W., Int. J. Pharm. 185:129-88 (1999) and Wang W., Int. J. Pharm. 203:1-60 (2000).

In certain embodiments, the presently disclosed formulations comprise a buffer. As used herein, the term "buffer" is intended to mean a substance that stabilizes the pH of a liquid, either its acidity or alkalinity. In other words, a buffered solution resists changes in pH by the action of its acid-base conjugate components. The term as it is used herein is intended to refer to a solution having a buffering substance, such as an acid, in equilibrium with its conjugate base. A buffer can provide optimal buffer capacity in the region of their $pK_a$, where buffer capacity refers to a resistance to change in pH when perturbed with either acid or base added to the solution. In certain embodiments, the presently disclosed formulations have a pH in the range from about 5.0 to about 7.5, in some of these embodiments from about 5.8 to about 6.8, for example from about 6.0 to about 6.4, and in certain embodiments has a pH of about 6.2. Non-limiting examples of buffers that will control the pH in this range include acetate, succinate, succinate, gluconate, histidine, citrate, glycylglycine and other organic acid buffers.

In some embodiments, the buffer of the presently disclosed formulations is a histidine buffer. A histidine buffer is a buffer comprising histidine ions. Non-limiting examples of histidine buffers include L-histidine and its conjugate acid L-histidine hydrochloride, as well as histidine acetate, histidine phosphate, histidine sulfate. In certain embodiments, the buffer is L-histidine/L-histidine hydrochloride. In these embodiments, useful concentrations of L-histidine/L-histidine hydrochloride are from about 1.0 mM to about 3.0 mM L-histidine and from about 1.5 mM to about 3.0 mM L-histidine hydrochloride. In particular embodiments, the concentration of L-histidine is from about 1.5 mM to about 2.5 mM and the concentration of L-histidine hydrochloride is from about 2.0 mM to about 2.5. In certain embodiments, the concentration of L-histidine is about 1.93 mM and the concentration of L-histidine hydrochloride is about 2.23 mM. Other non-limiting exemplary buffers include an acetic acid or acetate buffer, a glutamic acid or glutamate buffer, a succinic acid or succinate buffer, or a propionic acid or propionate buffer.

In some embodiments, the subject matter described herein is directed to a pharmaceutical formulation comprising trastuzumab, sorbitol, L-Histidine, L-Histidine HCl and PEG 3350, wherein the molar ratio of said sorbitol to said trastuzumab is about 631 mole sorbitol:about 1 mole trastuzumab.

In some embodiments, the subject matter described herein is directed to a pharmaceutical formulation comprising trastuzumab, sorbitol, L-Histidine, L-Histidine HCl and PEG 3350, wherein the molar ratio of said sorbitol to said trastuzumab is about 631 mole sorbitol:about 1 mole trastuzumab, and wherein the molar ratio of PEG 3350 to the antibody is about 10:1.

In some embodiments, the subject matter described herein is directed to a pharmaceutical formulation comprising sorbitol, PEG 3350, protein and buffer such that sorbitol and protein is in molar ratio of 631 mole:1 mole and PEG 3350 to protein is in the molar ratio of 10 mole:1 mole and the formulation which is subsequently lyophilised is found to be stable at 2-8 degrees Celsius for at least 4 years.

In specific embodiments, the subject matter described herein is directed to a pharmaceutical formulation comprising, about 150 mg of an anti-HER2 monoclonal antibody; a buffer comprising about 2.16 mg of L-Histidine and 3.36 mg of L-Histidine HCl; about 115.2 mg sorbitol; about 33.6 mg PEG 3350; and about 7.2 mL sterile water for injection.

In another embodiment, the subject matter described herein is directed to a pharmaceutical formulation (which can be lyophilized) comprising, about 150 mg of an anti-HER2 monoclonal antibody; a buffer comprising about 2.16 mg of L-Histidine and 3.36 mg of L-Histidine HCl; about 115.2 mg sorbitol; and about 33.6 mg PEG 3350.

In some of these embodiments, the anti-HER2 monoclonal antibody comprises a $V_H$ domain having the sequence set forth in SEQ ID NO: 3 and a $V_L$ domain having the sequence set forth in SEQ ID NO: 4. In particular embodiments, the anti-HER2 monoclonal antibody is trastuzumab and thus has the heavy chain sequence set forth in SEQ ID NO: 1 and the light chain sequence set forth in SEQ ID NO: 2.

In specific embodiments, the subject matter described herein is directed to a pharmaceutical formulation comprising, about 150 mg of trastuzumab; a buffer comprising about 2.16 mg of L-Histidine and 3.36 mg of L-Histidine HCl; about 115.2 mg sorbitol; about 33.6 mg PEG 3350; and about 7.2 mL sterile water for injection.

In another specific embodiment, the subject matter described herein is directed to a pharmaceutical formulation (which can be lyophilized) comprising, about 150 mg of trastuzumab; a buffer comprising about 2.16 mg of L-Histidine and 3.36 mg of L-Histidine HCl; about 115.2 mg sorbitol; and about 33.6 mg PEG 3350.

Other excipients, such as bulking agents may also be present although in the most preferred embodiments sorbitol/PEG mixture are present as lyoprotectant and bulking agents. A "bulking agent" is a compound which adds mass to the lyophilized mixture and contributes to the physical structure of the lyophilized cake (e.g. facilitates the production of an essentially uniform lyophilized cake which maintains an open pore structure).

Exemplary bulking agents include mannitol and glycine. Sugar alcohols, also known as a polyols, polyhydric alcohols, or polyalcohols, are hydrogenated forms of carbohydrate having a carbonyl group reduced to a primary or secondary hydroxyl group. Polyols can be used as stabilizing excipients and/or isotonicity agents in both liquid and lyophilized formulations. While the presently disclosed formulations comprise sorbitol, additional polyols may be present within the formulation and can serve to protect polypeptides from both physical and chemical degradation pathways. Non-limiting examples of other sugar alcohols include glycerol, mannitol, xylitol, maltitol, lactitol, erythritol and threitol.

Other excipients include, for example, sugars such as sucrose, lactose or dextrose; salts such as NaCl, KCl or calcium phosphate, amino acids such as glycine, methionine or glutamic acid, surfactants, metal ions, buffer salts, chloride, propionate, acetate or succinate, preservatives and polypeptides such as human serum albumin, as well as saline and water.

Generally, the liquid formulations are isotonic. By "isotonic" is meant that the formulation has essentially the same osmotic pressure as human blood. Isotonicity can be measured using a vapor pressure or ice-freezing type osmometer, for example.

The presently disclosed formulations are stable. A "stable" formulation is one in which the protein therein essentially retains its physical and chemical stability and integrity upon storage. Stability can be measured at a selected temperature for a selected time period. For rapid screening, the formulation may be kept at 40° C. for 2 weeks to 1 month, at which time stability is measured. Where the formulation is to be stored at 2-8° C., in some embodiments, the formulation is stable for at least six months. In other embodiments, the formulations are stable for at least 9 months upon storage at about 2° C. to about 8° C. In certain embodiments, the formulations are stable for at least four years upon storage at about 2° C. to about 8° C.

The extent of aggregation following lyophilization and storage can be used as an indicator of protein stability. For example, a "stable" formulation may be one wherein less than about 10% and preferably less than about 5% of the protein is present as an aggregate in the formulation. An increase in aggregate formation following lyophilization and storage of the lyophilized formulation can be determined. For example, a "stable" lyophilized formulation may be one wherein the increase in aggregate in the lyophilized formulation is less than about 5% and in some embodiments, less than about 3%, when the lyophilized formulation is stored at 2-8° C. for at least four year. In other embodiments, stability of the protein formulation may be measured using a biological activity assay.

Various other stability assays are available to the skilled practitioner for confirming the stability of the formulation and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be tested by evaluating physical stability, chemical stability, and/or biological activity of the antibody in the formulation around the time of formulation as well as following storage at the noted temperatures. Physical and/or chemical stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may result in aggregation, deamidation (e.g. Asn deamidation), oxidation (e.g. Met oxidation), isomerization (e.g. Asp isomeriation), clipping/hydrolysis/fragmentation (e.g. hinge region fragmentation), succinimide formation, unpaired cysteine(s), N-terminal extension, C-terminal processing, glycosylation differences, etc. Biological activity or antigen binding function can be evaluated using various techniques available to the skilled practitioner. Freezing of the formulation is specifically contemplated herein. Hence, the formulation can be tested for stability upon freezing and thawing.

II. Methods of Preparing Pharmaceutical Formulations

The invention also provides a method of making a pharmaceutical formulation comprising preparing the formulation as described herein, and in some embodiments, evaluating physical stability, chemical stability, or biological activity of the protein (e.g., antibody) in the formulation.

In an embodiment there is provided a process for preparing a stable formulation, comprising the steps of:
a) mixing protein, PEG and sorbitol such that sorbitol:protein is in molar ration of range of 550-700 mole sorbitol:1 mole of protein; and PEG:protein is in molar ratio of 2-50 mole:1 mole;
b) lyophilizing the mixture; and optionally
c) reconstituting the lyophilized mixture of step (b) in a diluent such that the protein concentration is from 5 mg/ml to 50 mg/ml.

In the above process the lyophilized mixture may further comprise of a bulking agent.

In another embodiment there is provided a process for preparing a stable formulation, comprising the steps of:
a) mixing protein and sorbitol, in the molar ratio of sorbitol:protein in a range of 550-700 mole sorbitol:1 mole of protein; and
b) adding PEG to the mixture (a) in a molar ratio of PEG:protein in a range of 2:1 to 50:1, preferably is 10:1;
c) diluting the above mixture to form liquid formulation.

In certain embodiments, the subject matter described herein is directed to methods of preparing a formulation comprising the steps of: a) lyophilizing a mixture comprising a protein (e.g., an antibody); sorbitol, wherein the molar ratio of said sorbitol to said protein (e.g., antibody) is about 550 to about 700 mole sorbitol:about 1 mole protein (e.g., antibody); and polyethylene glycol (PEG), wherein the molar ratio of PEG to protein (e.g., antibody) is in a range of about 2:1 to 50:1.

In certain embodiments, the subject matter described herein is directed to methods of preparing a formulation comprising the steps of: a) lyophilizing a mixture comprising a protein (e.g., an antibody); sorbitol, wherein the molar ratio of said sorbitol to said protein (e.g., antibody) is about 550 to about 700 mole sorbitol:about 1 mole protein (e.g., antibody); and polyethylene glycol (PEG), wherein the molar ratio of PEG to protein (e.g., antibody) is in a range of about 2:1 to 50:1; and (b) reconstituting the lyophilized mixture of step (a) in a diluent such that the protein (e.g., antibody) concentration is from about 5 mg/mL to about 50 mg/mL. In some embodiments, the protein (e.g., antibody) is present at a concentration of about 10 mg/mL to about 40 mg/mL. In other embodiments, the protein (e.g., antibody) is present at a concentration of about 15 mg/mL to about 35 mg/mL. In still other embodiments, the protein (e.g., antibody) is present at a concentration of about 21 mg/mL. Useful concentrations of protein (e.g., antibody) also include from about 0.10 mM to about 0.25 mM; from about 0.15 mM to about 0.18 mM; and about 0.167 mM.

In certain embodiments, the subject matter described herein is directed to methods of preparing a formulation comprising the steps of: a) lyophilizing a mixture comprising an anti-HER2 antibody; sorbitol, wherein the molar ratio of said sorbitol to said antibody is about 550 to about 700 mole sorbitol:about 1 mole antibody; and polyethylene glycol (PEG), wherein the molar ratio of PEG to protein (e.g., anti-HER2 antibody) is in a range of about 2:1 to 50:1.

In certain embodiments, the subject matter described herein is directed to methods of preparing a formulation comprising the steps of: a) lyophilizing a mixture comprising an anti-HER2 antibody; sorbitol, wherein the molar ratio of said sorbitol to said antibody is about 550 to about 700 mole sorbitol:about 1 mole antibody; polyethylene glycol (PEG), wherein the molar ratio of PEG to protein (e.g., antibody) is in a range of about 2:1 to 50:1; and (b) reconstituting the lyophilized mixture of step (a) in a diluent such that the antibody concentration is from about 5 mg/mL to about 50 mg/mL. In some embodiments, the antibody is present at a concentration of about 10 mg/mL to about 40 mg/mL. In other embodiments, the antibody is present at a concentration of about 15 mg/mL to about 35 mg/mL. In still other embodiments, the antibody is present at a concentration of about 21 mg/mL.

In certain embodiments, the subject matter described herein is directed to methods of preparing a formulation comprising the steps of: a) lyophilizing a mixture comprising trastuzumab; sorbitol, wherein the molar ratio of said sorbitol to said trastuzumab is about 550 to about 700 mole sorbitol:about 1 mole trastuzumab; and polyethylene glycol (PEG), wherein the molar ratio of PEG to protein (e.g., trastuzumab) is in a range of about 2:1 to 50:1.

In certain embodiments, the subject matter described herein is directed to methods of preparing a formulation comprising the steps of: a) lyophilizing a mixture comprising trastuzumab; sorbitol, wherein the molar ratio of said sorbitol to said trastuzumab is about 550 to about 700 mole sorbitol:about 1 mole trastuzumab; and polyethylene glycol (PEG), wherein the molar ratio of PEG to protein (e.g., trastuzumab) is in a range of about 2:1 to 50:1; and (b) reconstituting the lyophilized mixture of step (a) in a diluent such that the trastuzumab concentration is from about 5 mg/mL to about 50 mg/mL. In some embodiments, the trastuzumab is present at a concentration of about 10 mg/mL to about 40 mg/mL. In other embodiments, the trastuzumab is present at a concentration of about 15 mg/mL to about 35 mg/mL. In still other embodiments, the trastuzumab is present at a concentration of about 21 mg/mL.

In specific embodiments, the formulation comprises PEG-3350, e.g., as described herein. For example, the formulation comprises trastuzumab, sorbitol, L-Histidine, L-Histidine HCl and PEG 3350, wherein the molar ratio of said sorbitol to said trastuzumab is about 631 mole sorbitol:about 1 mole trastuzumab, and wherein the molar ratio of PEG 3350 to the antibody is about 10:1.

In some embodiments, the formulation comprises a buffer, e.g., histidine and/or histidine-HCl, e.g., as described herein.

In one example, the formulation comprises about 150 mg of trastuzumab; a buffer comprising about 2.16 mg of L-Histidine and 3.36 mg of L-Histidine HCl; about 115.2 mg sorbitol; and about 33.6 mg PEG 3350

For biological drugs, formulation ingredients are typically introduced via tangential flow filtration (TFF). In this process, the drug substance (DS) is exchanged into the formulation buffer containing added excipients but lacking surfactant (e.g., polyethylene glycol). The DS is concentrated to higher values than the target DS concentration. Dilution is then performed where surfactant is added and the concentration is adjusted to the target set-point.

As is known in the art, the process of TFF involves repeated cycling of the drug substance across a membrane multiple times using the target base buffer. This cycling could potentially damage the protein and cause physical degradation resulting in high aggregates. Sugars in the formulation typically offer protection if such a damage were to occur. TFF with sugar, however, typically requires a very high volume of formulation components.

An alternate procedure involving direct addition of excipients was developed using a common base buffer. This alternate process involves the direct addition of excipients to reduce raw material consumption by topping the sorbitol excipient instead of membrane based solution exchange into the bulk DS during formulation.

In certain embodiments, the pharmaceutical formulation is prepared as shown in FIG. 1. The process involves ultrafiltration followed by diafiltration (TFF) into the formulation buffer of His-His HCl at pH of 6. This is followed by viral filtration of the drug substance. Since liquid stocks of excipients are added during formulation, in order to prevent over-dilution of the drug substance, it is necessary that the protein concentration after viral filtration is not less than 32 mg/mL.

In an embodiment, preparation of the pharmaceutical formulation involves the following steps:

1. Preparation of Histidine buffer
2. Preparation of 1M Sorbitol and 50 mM PEG 3350 in Histidine buffer.
3. Adjusting pH of Sorbitol and PEG stock to 6.0 with 0.1 N HCl or 0.1 N NaOH
4. Addition of Sorbitol to a final concentration of 105.4 mM
5. Addition of PEG 3350 to a final concentration of 1.67 mM 6. Adjustment of the concentration of the protein to 25.00 mg/mL with histidine buffer.

7. Adjustment of the pH of the formulation to 6.00

III. Methods of Treatment

In particular embodiments, the subject matter disclosed herein is directed to a method of treating a HER2-overexpressing cancer in a subject comprising, administering a formulation of the disclosure, e.g., comprising about 150 mg of an anti-HER2 monoclonal antibody; a buffer comprising about 2.16 mg of L-Histidine and 3.36 mg of L-Histidine HCl; about 115.2 mg sorbitol; about 33.6 mg PEG 3350; and about 7.2 mL sterile water to the subject. In one example, the formulation comprises about 150 mg of trastuzumab; a buffer comprising about 2.16 mg of L-Histidine and 3.36 mg of L-Histidine HCl; about 115.2 mg sorbitol; about 33.6 mg PEG 3350; and about 7.2 mL sterile water to the subject.

The method is particularly suited for the treatment of cancer wherein the subject may also be receiving a chemotherapeutic agent and/or another anti-HER2 antibody, e.g., pertuzumab. Exemplary chemotherapeutic agents are doxorubicin, cyclophosphamide and either paclitaxel or Docetaxel or Docetaxel and carboplatin or an anthracycline or paclitaxel or capecitabine and/or 5-fluorouracil.

In one example, the cancer is breast cancer. For example, the cancer is HER2 overexpressing breast cancer. For example, the breast cancer is metastatic breast cancer.

In one example, the methods is for adjuvant treatment of breast cancer.

In one example, the cancer is gastric cancer, for example metastatic gastric cancer.

Depending on the type and severity of the disease, about 1 μg/kg to 50 mg/kg (e.g. 0.1-20 mg/kg) of protein is an initial candidate dosage for administration to the patient, whether, for example, by one or more separate administrations, or by continuous infusion. In some embodiments, the dosage of the protein will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the protein). An initial higher loading dose, followed by one or more lower doses may be administered. In one embodiment, the protein is administered as a loading dose of approximately 840 mg followed by approximately 420 mg approximately every 3 weeks. In another embodiment, the protein is administered as a dose of approximately 1050 mg administered approximately every 3 weeks. For example, the protein (e.g., anti-HER2 antibody, e.g., trastuzumab) is administered at loading dose of about 4 mg/kg followed by a maintenance dose each week of about 2 mg/kg. For example, the protein (e.g., anti-HER2 antibody, e.g., trastuzumab) is administered at loading dose of about 8 mg/kg followed by a maintenance dose every three weeks of about 4 mg/kg.

In some embodiments, the protein composition is administered by intravenous, intramuscular or subcutaneous routes and in particular embodiments, by an intravenous route.

IV. Articles of Manufacture/Pharmaceutical Kit

In another embodiment of the invention, an article of manufacture or a pharmaceutical kit is provided which comprises the pharmaceutical formulation described herein in a container and in some embodiments, further provides instructions for its use. Suitable containers include, for example, bottles, vials (e.g. dual chamber vials), syringes (such as dual chamber syringes) and test tubes. The container may be formed from a variety of materials such as glass or plastic. In some embodiments, the formulation is provided inside a vial with a stopper pierceable by a syringe, generally in aqueous form. The vial is desirably stored at about 2-8° C. until it is administered to a subject in need thereof. The vial may for example be a 10-15 cc vial. The container holds the formulation and the label on, or associated with, the container may indicate directions for use. The container holding the formulation may be a multi-use vial, which allows for repeat administrations (e.g. from 2-6 administrations) of the reconstituted formulation. The article of manufacture or the pharmaceutical kit may further include other materials desirable from a commercial and user standpoint, including other buffers, diluents, filters, needles, syringes, and package inserts with instructions for use as noted in the previous section.

The formulations can be prepared in convenient dosages that contain specific amounts of protein. In some embodiments, the amount of protein is about 10 mg to about 500 mg; or about 300 mg to about 500 mg; or about 400 mg to about 480 mg; or about 440 mg. In some embodiments, the amount of protein is about 50 mg to about 300 mg. In other embodiments, the amount of protein is 100 mg to about 200 mg. In still other embodiments, the amount of protein is about 130 mg to about 170 mg. In certain embodiments, the amount of protein is about 150 mg.

In some embodiments, the reconstituted formulation or lyophilized formulation is contained within a vessel such as a stoppered vial for ease of use. Thus, in an embodiment, the subject matter described herein is directed to a vial comprising a pharmaceutical formulation, said formulation comprising, about 150 mg of an anti-HER2 monoclonal antibody; a buffer comprising, about 2.16 mg of L-Histidine and 3.36 mg of L-Histidine HCl; about 115.2 mg sorbitol; and about 33.6 mg PEG 3350. In this embodiment, the vial can further comprise a diluent. In certain embodiments, the diluent is sterile water, and in some of these embodiments, bacteriostatic water for injection (BWFI). The volume of sterile water is preferably about 7.2 mL.

In another embodiment, the article of manufacture or the pharmaceutical kit comprises: (a) a container which holds a lyophilized mixture comprising the protein (e.g., antibody); sorbitol, present in a molar ratio of about 550 to about 750 mole of sorbitol to about 1 mole of protein (e.g., antibody); and polyethylene glycol (PEG), wherein the molar ratio of PEG to protein (e.g., trastuzumab) is in a range of about 2:1 to 50:1;

and (b) instructions for reconstituting the lyophilized mixture with a diluent. The article of manufacture or the pharmaceutical kit may further comprise a second container which holds a diluent (e.g. bacteriostatic water for injection (BWFI)).

The present subject matter is further described herein by the following non-limiting examples which further illustrate the invention, and are not intended, nor should they be interpreted to, limit the scope of the invention.

EXAMPLES

1. Lyophilization and Analysis of Cake Morphology i. PEG Formulation

A formulation that contains only PEG was prepared in two different concentrations according to Table 1A and 1B. The PEG-containing formulation was lyophilized and the cake morphology and structure was examined after storing at stress condition of 40° C.±2° C. (75%±5% R.H). Evaluation of the formulation involved lyophilizing 150 mg of formulated bulk drug substance composition according to Table 1A and Table 1B in 15 mL vials. The vials were half-stoppered using coated chloro-butyl igloo stoppers and lyophilized. Both test formulations containing 37.5-fold and 100-fold molar excess of PEG3350 to the Antibody lyophilized with no collapse and well formed cake structure. The resultant lyophilized cakes were placed at 40° C.±2° C. (75%±5% R.H. chamber for 3 weeks after which time the cake morphology was re-examined. The visual appearance of the cake was analyzed at initial time as well as after 3 weeks at 40° C.±2° C. (75%±5% R.H).

TABLE 1A

Formulation 3

| Component | Amount (mg) present per vial | Conc (mM) per vial | Molar excess of PEG3350 to antibody |
|---|---|---|---|
| Trastuzumab | 150 | 0.2 | 37.5 |
| L-Histidine | 6.44 | 5 | |
| PEG 4000 | 150 | 7.5 | |
| Formulation pH adjusted to 6.0 | | | |

TABLE 1B

Formulation 4

| Component | Amount (mg) present per vial | Conc (mM) per vial | Molar excess of PEG3350 to antibody |
|---|---|---|---|
| Trastuzumab | 150 | 0.2 | 100 |
| L-Histidine | 6.44 | 5 | |
| PEG 4000 | 400 | 20 | |
| Formulation pH adjusted to 6.0 | | | |

The lyophilized cake of formulation 3 was examined at initial time T0 and after storing at 40° C.±2° C. (75%±5% R.H) for three weeks (T3W 40° C.). Formulation 3 could not maintain cake structure when stored at accelerated stability condition of 40° C.±2° C. (±5% R.H) for 3 weeks as evidenced by the collapse in the cake structure.

The lyophilized cake of formulation 4 was examined at initial time T0 and after storing at 40° C.±2° C. (±5% R.H) for three weeks (T3W 40° C.). The formulation could not maintain cake structure when stored at accelerated stability condition of 40° C.±2° C. (±5% R.H) for 3 weeks as evidenced by the collapse in the cake structure.

ii. PEG/Sorbitol Formulations

Formulations containing a combination of PEG and Sorbitol were evaluated. Four different molar excess ratios of PEG and Sorbitol to antibody were evaluated: 36, 100, 310 and 667. In addition to monitoring the cake morphology, product quality attributes such as physical stability by SEC, chemical stability by IEX, total protein content by UV 280, pH strength and osmolality were evaluated upon storage at 40° C. for 3 weeks.

5 mL of the formulated bulk drug substance according to Tables 2A, 2B, 2C and 2D were filled into a 15 mL vial. The vials were half-stoppered using coated chloro-butyl igloo stoppers and lyophilized. The resulting lyophilized cakes were analyzed immediately for product quality attributes at initial time T0 and also after storing at 40° C.±2° C. (75%±5% relative humidity) chamber for 3 weeks.

TABLE 2A

Formulation 6

| Component | Amount (mg) present per vial | Concentration in mM per vial | Molar excess of PEG3350 and Sorbitol to antibody |
|---|---|---|---|
| Trastuzumab | 150 | 0.2 | 667 |
| L-Histidine | 6.44 | 5 | |
| L-Methionine | 0.75 | 1 | |
| PEG 3350 | 120 | 7.2 | |
| Sorbitol | 115 | 126.2 | |
| Formulation pH adjusted to 6.0 | | | |

TABLE 2B

Formulation 7

| Component | Amount (mg) present per vial | Concentration in mM per vial | Molar excess of PEG3350 and Sorbitol to antibody |
|---|---|---|---|
| Trastuzumab | 150 | 0.2 | 310 |
| L-Histidine | 6.44 | 5 | |
| L-Methionine | 0.75 | 1 | |
| PEG 3350 | 120 | 7.2 | |
| Sorbitol | 50 | 54.9 | |
| Formulation pH adjusted to 6.00 | | | |

TABLE 2C

Formulation 8

| Component | Amount (mg) present per vial | Concentration in mM per vial | Molar excess of PEG3350 and Sorbitol to antibody |
|---|---|---|---|
| Trastuzumab | 150 | 0.2 | 100 |
| L-Histidine | 6.44 | 5 | |
| L-Methionine | 0.75 | 1 | |
| PEG 3350 | 120 | 7.2 | |
| Sorbitol | 11.7 | 12.8 | |
| Formulation pH adjusted to 6.00 | | | |

TABLE 2D

Formulation 9

| Component | Amount (mg) present per vial | Concentration in mM per vial | Molar excess of PEG3350 to antibody |
|---|---|---|---|
| Trastuzumab | 150 | 0.2 | 36 |
| L-Histidine | 6.44 | 5 | |
| L-Methionine | 0.75 | 1 | |
| PEG 3350 | 150 | 7.5 | |
| Formulation pH adjusted to 6.0 | | | |

All formulations containing both PEG and sorbitol provided improved cake structure and increased physical stability at elevated temperatures compared to the PEG-only formulations.

2. Stability of PEG/Sorbitol Formulations

The lyophilized drug product cakes were reconstituted with 7.2 mL of water for injection and analyzed for the pH of the formulation, size variants distribution via SEC and charged variant distribution via LEX at initial time and after Storage for 3 weeks at 40° C. The data in Table 3 show that the four test formulations have stable pH of approximately 6.00 at time T0 and after storing at 40° C. for 3 weeks.

TABLE 3

| Formulation | pH at T0 | pH at T3 W, 40° C. |
|---|---|---|
| 6 | 6.02 | 6.12 |
| 7 | 6.04 | 6.07 |
| 8 | 6.00 | 6.09 |
| 9 | 5.98 | 6.18 | i. Physical Stability

Figure 2:
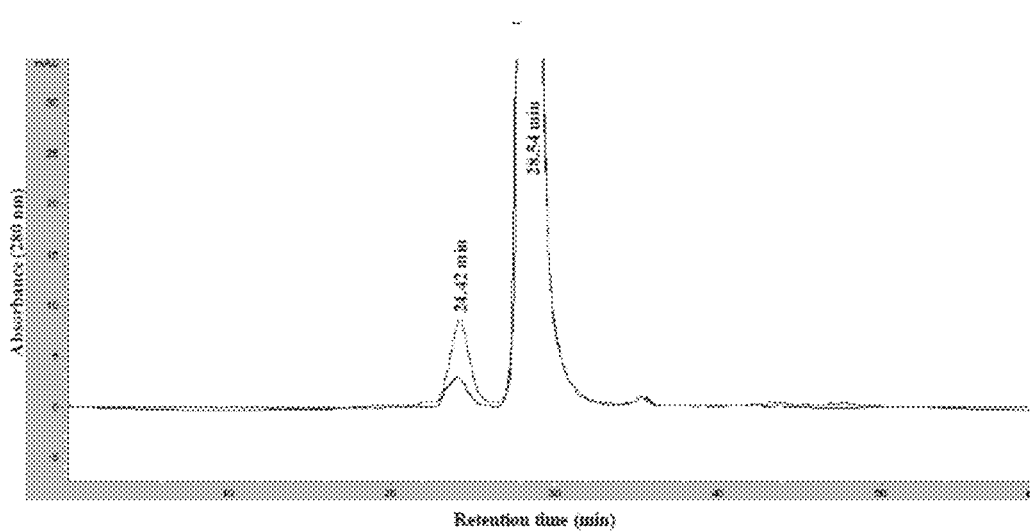

FIG. 2 is a representative SEC chromatogram of test formulation 6. The monomer fraction elutes at 28.54 min and the aggregate elutes at 24.42 minutes. An increase in the aggregate is seen in sample stored at 40° C. for 3 weeks (red trace, arrow) when compared to the sample at initial condition (blue trace).

Table 4 summarizes the data for the physical stability of test formulations at T0 and after storage at 40° C. for three weeks following reconstitution.

TABLE 4

| Sample | Ratio of PEG and Sorbitol to antibody | Time-point | % HMWP | % Monomer | % LMWP |
|---|---|---|---|---|---|
| Form 6 | PEG:36x excess Sorbitol:631x excess | T0 T3 W at 40° C. | 0.75 3.40 | 99.04 96.28 | 0.21 0.32 |
| Form 7 | PEG:36x excess Sorbitol:274 | T0 T3 W at 40° C. | 0.94 3.81 | 98.81 95.64 | 0.25 0.55 |
| Form 8 | PEG:36 x excess Sorbitol:64 | T0 T3 W at 40° C. | 0.79 4.78 | 98.99 94.67 | 0.22 0.54 |
| Form 9 | PEG:36 x excess Sorbitol:0 | T0 T3 W at 40° C. | 0.93 5.59 | 98.85 93.78 | 0.21 0.63 |

Figure 3:
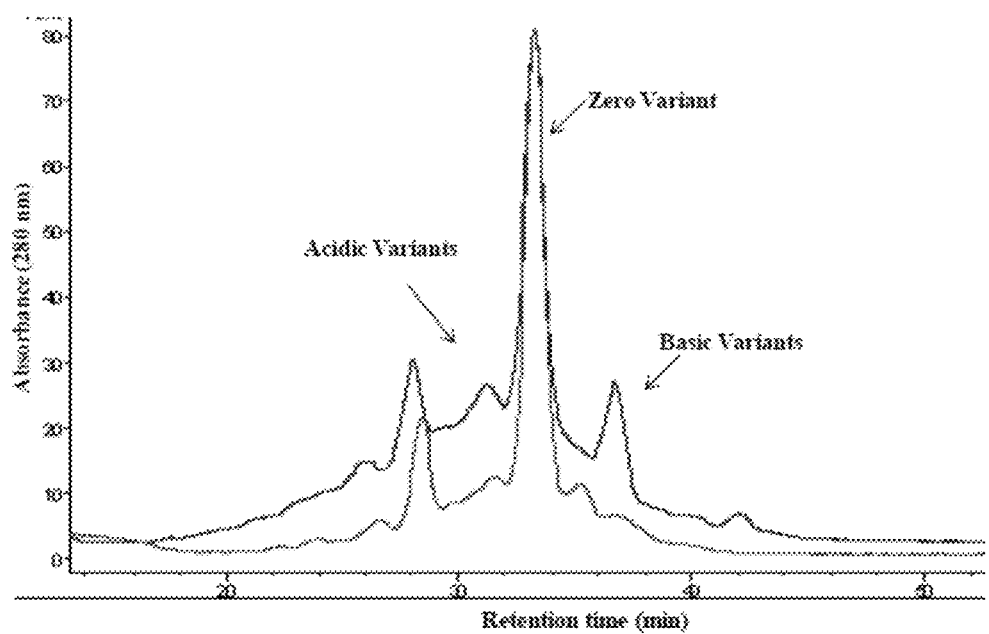

FIG. 3 is a representative IEX chromatogram of test formulation 6.

ii. Chemical Stability

Table 5 summarizes the data for the chemical stability of test formulations at T0 and after storage at 40° C. for three weeks following reconstitution.

TABLE 5

| Sample | Ratio of PEG and Sorbitol to antibody | Time-point | % Acidic | % Zero | % Basic |
|---|---|---|---|---|---|
| Form 6 | PEG:36x excess Sorbitol:631x excess | T0 T3 W at 40° C. | 45.64 46.78 | 37.01 32.29 | 17.35 20.93 |
| Form 7 | PEG:36x excess Sorbitol:274 | T0 T3 W at 40° C. | 42.54 43.92 | 35.52 35.48 | 21.94 20.60 |
| Form 8 | PEG:36 x excess Sorbitol:64 | T0 T3 W at 40° C. | 42.27 46.30 | 35.08 35.20 | 22.64 18.51 |
| Form 9 | PEG:36 x excess Sorbitol:0 | T0 T3 W at 40° C. | 46.15 45.63 | 30.98 34.66 | 22.87 19.71 |

The four formulations were comparable in terms of appearance, pH and chemical stability at initial time as well as after storing at 40° C. for three weeks. However, significant differences could be observed in the physical stability of the test formulations as determined by SEC. A summary of the analysis of the physical stability data is represented in Table 6 showing that Formulation 6 is superior. A correlation between the amount of sorbitol and the physical stability is evident wherein formulations with a larger proportion of sorbitol afforded greater stability to the drug product.

TABLE 6

| Category | Ranking of Formulations |
|---|---|
| Appearance | 6 = 7 = 8 = 9 |
| pH of solution | 6 = 7 = 8 = 9 |
| Size variants based on SEC | 6 > 7 > 8 > 9 |
| Charged variants based on IEX | 6 = 7 = 8 = 9 |

3. Liquid State Studies

The effect of molar excess PEG/sorbitol additive was assessed for type and extent of degradation. The experiment was conducted in a liquid state because higher degradation would be expected compared to the lyophilized state.

Liquid formulations were prepared at a concentration of 25 mg/mL of antibody and varying concentrations of the sorbitol/polymer additive corresponding to 0.167 mM protein.

TABLE 7

| Formulation | Components | Ratio of PEG + Sorbitol:Antibody |
|---|---|---|
| 13 (PEG only formulation, lyoprotectant:Ab < 100) | PEG3350 = 6.0 mM Sorbitol = 0 L-Methionine = 0.83 mM | 36:1 |
| 16 (PEG + Sorbitol:Ab < 100) | PEG3350 = 6.0 mM Sorbitol = 6.0 mM L-Methionine = 0.83 mM | 72:1 |
| 23 (PEG + Sorbitol:Ab > 100) | PEG3350 = 6.0 mM Sorbitol = 105.2 mM L-Methionine = 0.83 mM | 667:1 |
| 15 (Trehalose:Ab = 400) Herceptin ® Formulation | Trehalose = 66.7 mM Polysorbate 20 = 0.01% (w/v) | 400:1 |

Formulations 13, 16, 23 contained varying concentrations of the PEG/sorbitol additive. Formulation 15 containing trehalose is a control. To 2R vials was added 1 mL of the liquid formulations. The vials were stoppered, crimped and stored at 40° C. for 4 weeks. Samples were withdrawn at 2 week intervals and analyzed for physical stability by SEC (Table 8) and chemical stability by IEX (Table 10).

TABLE 8

Physical stability of the test formulations in liquid state under accelerated stability conditions.

| Formulation | Components | Time-point | % HMWP | % Monomer | % LMWP |
|---|---|---|---|---|---|
| 13 | PEG only | T0 | 1.32 | 98.31 | 0.37 |
| | | T2 W | 1.49 | 94.29 | 4.22 |
| | | T4 W | 1.61 | 89.89 | 8.51 |
| 16 | PEG + Sorbitol < 100:Ab | T0 | 0.91 | 98.76 | 0.33 |
| | | T2 W | 0.92 | 96.45 | 2.63 |
| | | T4 W | 0.89 | 95.45 | 3.66 |
| 23 | PEG + Sorbitol > 600:Ab | T0 | 0.90 | 98.86 | 0.24 |
| | | T2 W | 0.92 | 96.33 | 2.75 |
| | | T4 W | 1.00 | 97.14 | 1.86 |
| 15 | Trehalose (400x Ab) | T0 | 0.88 | 98.79 | 0.33 |
| | | T2 W | 0.88 | 96.58 | 2.54 |
| | | T4 W | 0.94 | 95.67 | 3.40 |

TABLE 9

Chemical stability of the test formulations in liquid state under accelerated stability conditions.

| Formulation | Components | Time-point | % Acidic | % Zero | % Basic |
|---|---|---|---|---|---|
| 13 | PEG only | T0 | 35.57 | 53.06 | 11.37 |
| | | T2 W | 61.74 | 22.49 | 15.77 |
| | | T4 W | 51.96 | 16.56 | 31.48 |
| 16 | PEG + Sorbitol < 100:Ab | T0 | 36.47 | 51.97 | 11.56 |
| | | T2 W | 49.22 | 30.43 | 20.35 |
| | | T4 W | 60.20 | 17.69 | 22.11 |
| 23 | PEG + Sorbitol > 600:Ab | T0 | 36.68 | 52.83 | 10.49 |
| | | T2 W | 47.18 | 26.64 | 26.18 |
| | | T4 W | 62.04 | 18.50 | 19.46 |
| 15 | Trehalose (400x Ab) | T0 | 36.21 | 52.72 | 11.07 |
| | | T2 W | 50.84 | 28.74 | 20.43 |
| | | T4 W | 58.16 | 18.28 | 23.56 |

The physical stability of the test formulations of the liquid screening experiments indicate that formulation 13 containing PEG was least stable displayed significant increase in fragmentation from 0.37% to 8.51% within 3 weeks at 40° C. All other test formulations namely 16 and 23 that contained varying proportions of sorbitol in addition to PEG had comparable physical stability.

Regarding chemical stability, all formulations degraded to some extent as evidenced by the higher proportions of acidic and basic variants when stored at 40° C. for 3 weeks.

4. Differential Scanning Calorimeter (DSC) Analysis

The formulations contained 150 mg of Trastuzumab at a concentration of 25 mg/mL. 5 mL of the formulated bulk DS was filled into 15 mL vials, half-stoppered with coated chloro-butyl igloo stoppers and lyophilized. The thermal stability of a formulation can be conveniently monitored via DSC. An increase in the temperature of melting of the test formulation is indicative of increased stability. Therefore the drug product from the formulation screening were analyzed via DSC. Table 10 shows components present in the formulations.

TABLE 10

Compilation of Tm1 and Tm2.

| Sample | Molar ratio of excipient to antibody | Tm1 (° C.) | Tm2 (° C.) |
|---|---|---|---|
| Herceptin B3372 | Trehalose:Mab = 384:1 Polysorbate 20 | 70.76* | 83.15** |
| Form 1 | Trehalose:Mab = 384:1 Polysorbate 20 | 71.61 | 83.01 |
| Form 6 | PEG:Mab = 35:1 Sorbitol:Mab = 631:1 | 71.29 | 82.69 |
| Form 8 | PEG:Mab = 35:1 Sorbitol:Mab = 55:1 | 71.14 | 82.67 |
| Form 26 | PEG:Mab = 10:1 Sorbitol:Mab = 80:1 | 72.22 | 82.82 |
| Form 27 | PEG:Mab = 10:1 Sorbitol:Mab = 631:1 | 72.06 | 83.08 |

Figure 4:
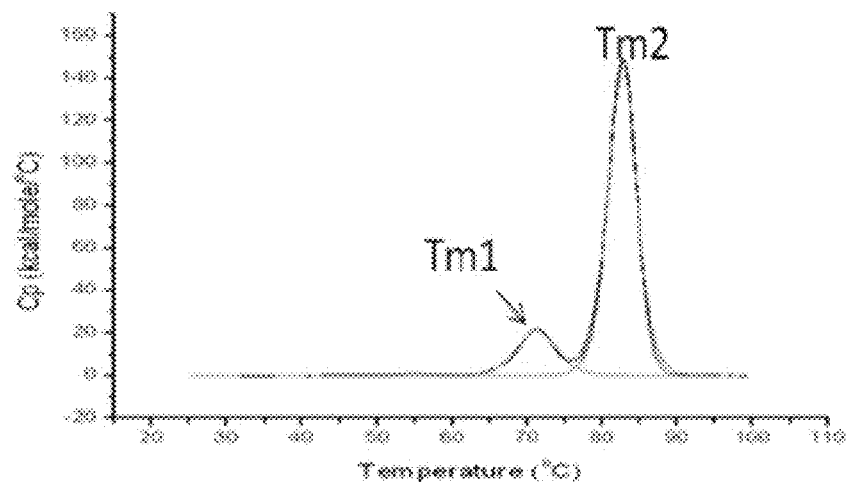
FIGS. 4-9 depict the thermal stability of formulations described herein as determined by DSC.
Figure 5:
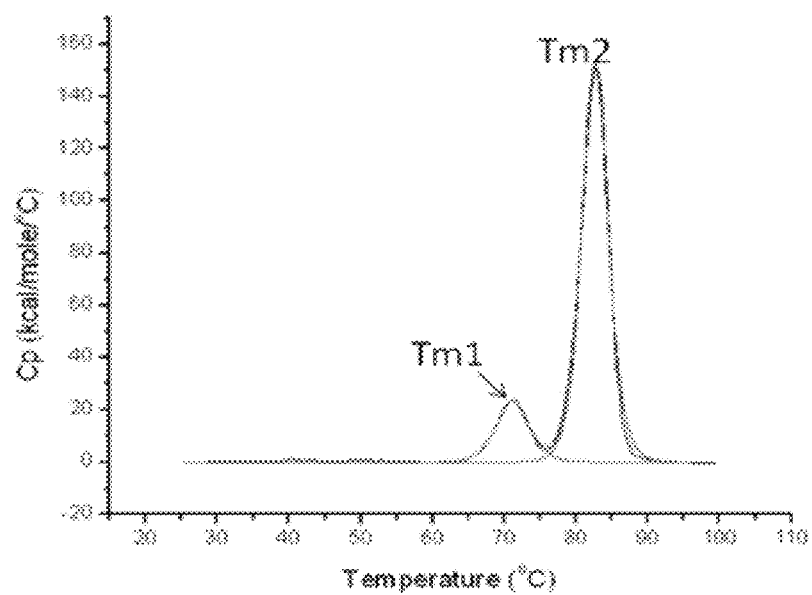
Figure 6:
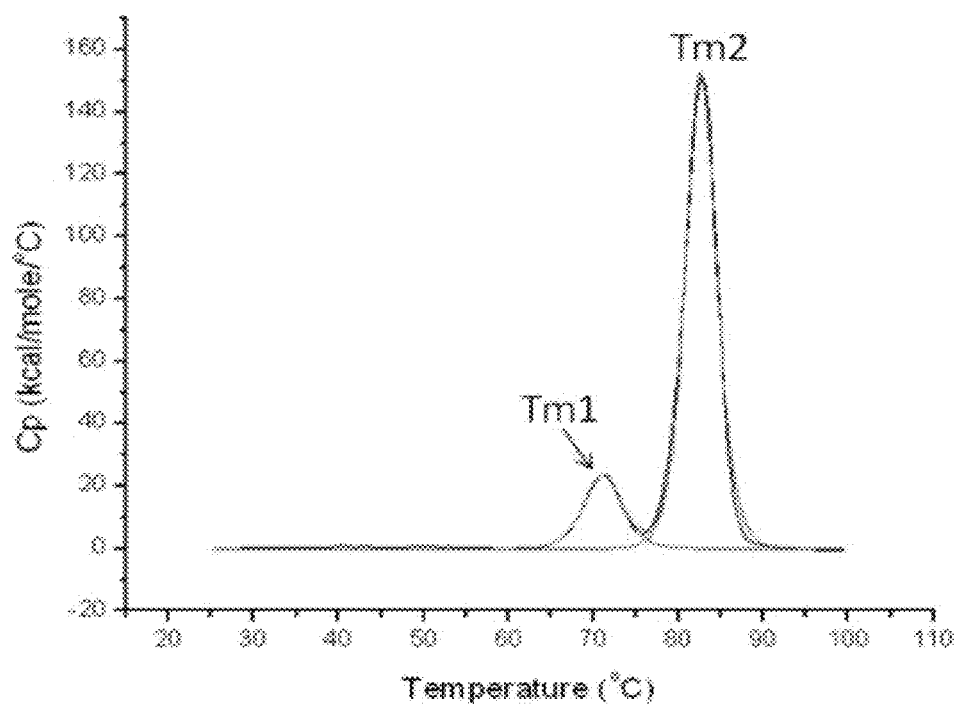
Figure 7:
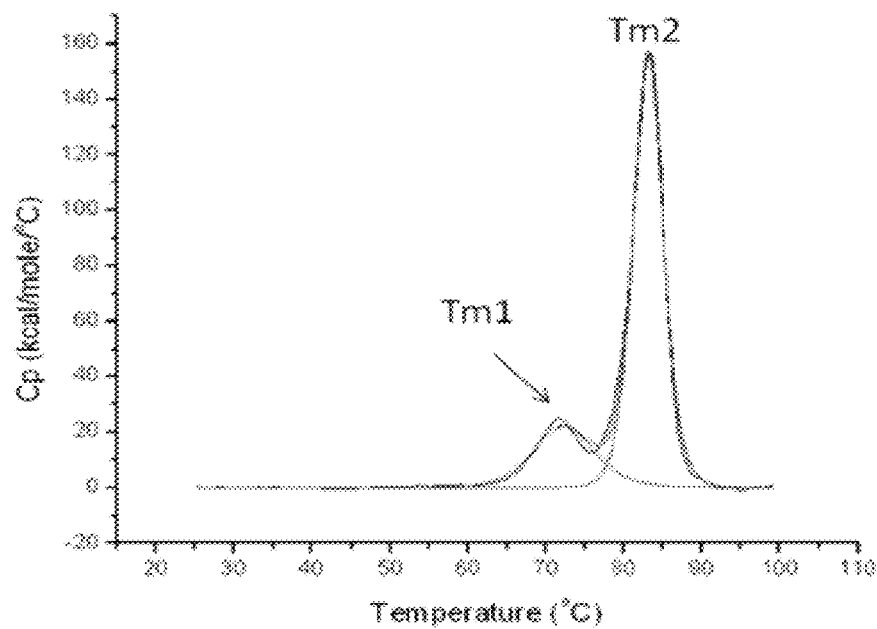
Figure 8:
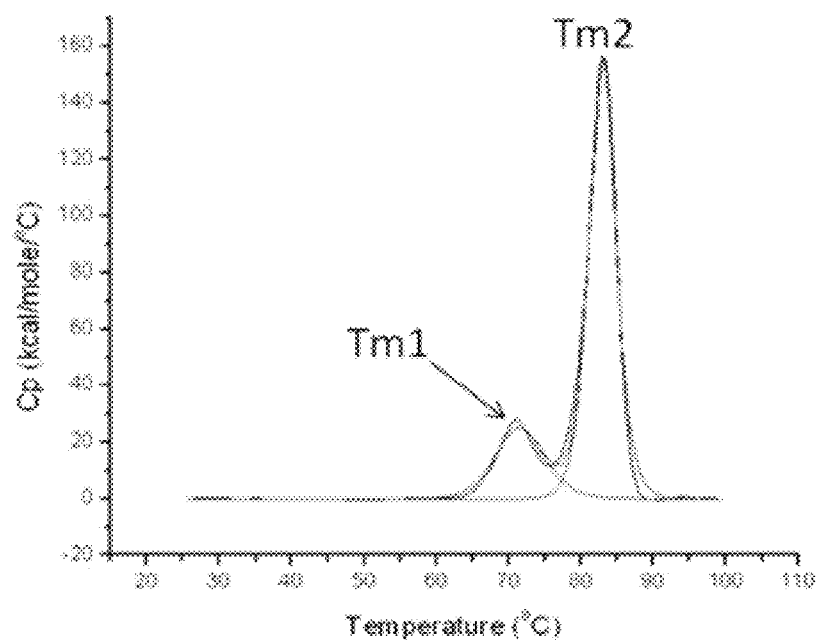
Figure 9:
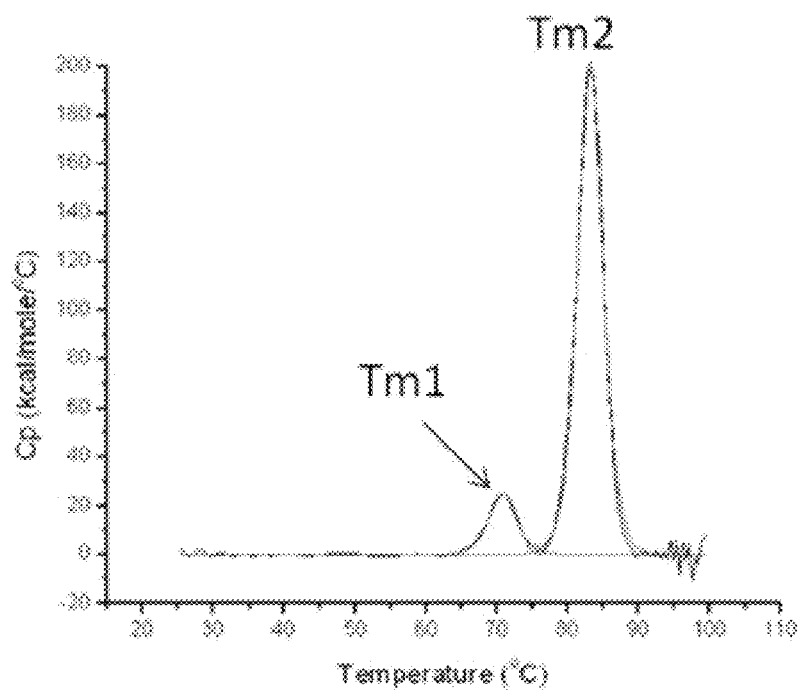

DSC analysis of the drug product of four test formulations (at 5 mg/mL diluted with the corresponding placebo) is shown in FIGS. 4-9. No significant difference was observed between the four test formulations based on temperature of melting for the first (Tm1) and the second transition (Tm2). FIG. 4 is a DSC of Formulation 6; FIG. 5 is a DSC of Formulation 8; FIG. 6 is a DSC of Formulation 26; FIG. 7 is a DSC of Formulation 27; FIG. 8 is a DSC of Formulation 1; and FIG. 9 is a DSC of Herceptin.

5. Short-Term Physical and Chemical Stability Studies on Lyophilized Formulations The four test formulations were subjected to a short term stability analysis. The lyophilized formulations are listed in Table 11.

TABLE 11

| Formulation No. | Components | Storage condition during stability study | Time-points for analysis | Techniques of analysis |
|---|---|---|---|---|
| 6 | PEG:Mab = 35:1 Sorbitol:Mab = 631:1 | 2-8° C. 25° C. ± 2° C. (65% ± 5% R.H.) 40° C. ± 2° C. (65% ± 5% R.H.) | T0, T1 M: 2-8° C., 25° C., 40° C. T2 M: 40° C. T3 M: 2-8° C., 25° C., 40° C. | Appearance of lyophilized cake and reconstituted solution, Moisture of the cake (only at initial time T0) UV280, pH, SEC, IEX |
| 8 | PEG:Mab = 35:1 Sorbitol:Mab = 55:1 | | | |
| 26 | PEG:Mab = 10:1 Sorbitol:Mab = 85:1 | | | Appearance of lyophilized cake and reconstituted solution, Moisture of the cake (only at initial time T0) UV280, pH, SEC, IEX |
| 27 | PEG:Mab = 10:1 Sorbitol:Mab = 631:1 | | | |
| 1 | Trehalose:Mab = 384:1 Polysorbate 20 = 0.01% (w/v) | | | |

The design of the stability program is detailed above. At each time-point, the lyophilized cake was reconstituted with 7.2 mL of water for injection and analyzed for product quality attributes (listed in the tables 12A-13E).

TABLE 12A

Physical stability of Formulation 6 as determined by SEC.

| Formulation/ Batch # | Time-point | Condition | % HMWP | % Monomer | % LMWP |
|---|---|---|---|---|---|
| 6 PEG3350:Ab = 35:1 Sorbitol:Ab = 631:1 | Pre-Lyo | | 1.30 | 98.60 | 0.11 |
| | T0 | T0 | 1.38 | 98.41 | 0.22 |
| | T1 M | 2-8° C. | 1.63 | 98.20 | 0.17 |
| | T3 M | 2-8° C. | 1.34 | 98.52 | 0.13 |
| | T1 M | 25° C. | 1.87 | 97.96 | 0.17 |
| | T3 M | 25° C. | 1.90 | 97.93 | 0.17 |
| | T1 M | 40° C. | 2.97 | 96.90 | 0.13 |

TABLE 12A-continued

Physical stability of Formulation 6 as determined by SEC.

| Formulation/Batch # | Time-point | Condition | % HMWP | % Monomer | % LMWP |
|---|---|---|---|---|---|
| | T2 M | 40° C. | 3.49 | 96.38 | 0.13 |
| | T3 M | 40° C. | 3.79 | 95.99 | 0.22 |

TABLE 12B

Physical stability of Formulation 8 as determined by SEC.

| Formulation # | Time-point | Condition | % HMWP | % Monomer | % LMWP |
|---|---|---|---|---|---|
| 8 | Pre-Lyo | | 1.34 | 98.54 | 0.13 |
| PEG3350:Ab = 35:1 | T0 | T0 | 1.46 | 98.37 | 0.18 |
| Sorbitol:Ab = 55:1 | T1 M | 2-8° C. | 1.93 | 97.91 | 0.16 |
| | T3 M | 2-8° C. | 1.64 | 98.18 | 0.18 |
| | T1 M | 25° C. | 2.72 | 97.15 | 0.13 |
| | T3 M | 25° C. | 2.80 | 97.03 | 0.16 |
| | T1 M | 40° C. | 5.73 | 94.09 | 0.18 |
| | T2 M | 40° C. | 6.37 | 93.36 | 0.27 |
| | T3 M | 40° C. | 6.84 | 92.75 | 0.41 |

TABLE 12C

Physical stability of Formulation 26 as determined by SEC.

| Formulation # | Time-point | Condition | % HMWP | % Monomer | % LMWP |
|---|---|---|---|---|---|
| 26 | Pre-Lyo | | 1.19 | 98.67 | 0.14 |
| PEG3350:Ab = 10:1 | T0 | T0 | 1.12 | 98.67 | 0.14 |
| Sorbitol:Ab = 80:1 | T1 M | 2-8° C. | 1.41 | 98.31 | 0.29 |
| | T3 M | 2-8° C. | 1.47 | 98.21 | 0.32 |
| | T1 M | 25° C. | 2.13 | 97.57 | 0.30 |
| | T3 M | 25° C. | 2.60 | 97.06 | 0.34 |
| | T1 M | 40° C. | 4.73 | 94.90 | 0.38 |
| | T2 M | 40° C. | 5.84 | 93.86 | 0.30 |
| | T3 M | 40° C. | 6.79 | 92.79 | 0.41 |

TABLE 12D

Physical stability of Formulation 27 as determined by SEC.

| Formulation # | Time-point | Condition | % HMWP | % Monomer | % LMWP |
|---|---|---|---|---|---|
| 27 | Pre-Lyo | | 1.11 | 98.60 | 0.29 |
| PEG3350:Ab = 10:1 | T0 | T0 | 1.11 | 98.62 | 0.27 |
| Sorbitol:Ab = 631:1 | T1 M | 2-8° C. | 1.17 | 98.56 | 0.28 |
| | T3 M | 2-8° C. | 1.03 | 98.59 | 0.38 |
| | T1 M | 25° C. | 1.42 | 98.27 | 0.31 |
| | T3 M | 25° C. | 1.55 | 98.15 | 0.30 |
| | T1 M | 40° C. | 2.50 | 97.16 | 0.34 |
| | T3 M | 40° C. | 3.83 | 95.82 | 0.79 |

TABLE 12E

Physical stability of Formulation 1 as determined by SEC.

| Formulation # | Time-point | Condition | % HMWP | % Monomer | % LMWP |
|---|---|---|---|---|---|
| 1 | Pre-Lyo | | 1.19 | 98.54 | 0.26 |
| | T0 | T0 | 1.18 | 98.53 | 0.26 |
| | T1 M | 2-8° C. | 1.24 | 98.49 | 0.27 |
| | T3 M | 2-8° C. | 1.15 | 98.60 | 0.24 |
| | T1 M | 25° C. | 1.55 | 98.20 | 0.25 |
| | T3 M | 25° C. | 1.71 | 98.03 | 0.25 |

TABLE 12E-continued

Physical stability of Formulation 1 as determined by SEC.

| Formulation # | Time-point | Condition | % HMWP | % Monomer | % LMWP |
|---|---|---|---|---|---|
| | T1 M | 40° C. | 2.45 | 97.28 | 0.27 |
| | T3 M | 40° C. | 3.50 | 96.22 | 0.27 |

TABLE 13A

Chemical stability of Formulation 6 as determined by IEX.

| Formulation/Batch # | Time-point | Condition | % Acidic | % Zero | % Basic |
|---|---|---|---|---|---|
| 6 | Pre-Lyo | | 34.27 | 56.65 | 9.09 |
| PEG3350:Ab = 35:1 | T0 | T0 | 31.68 | 61.47 | 6.85 |
| Sorbitol:Ab = 631:1 | T1 M | 2-8° C. | 31.27 | 63.02 | 5.71 |
| | T3 M | 2-8° C. | | | |
| | T1 M | 25° C. | 33.33 | 60.66 | 6.01 |
| | T3 M | 25° C. | 33.68 | 59.04 | 7.28 |
| | T1 M | 40° C. | 33.54 | 55.90 | 10.56 |
| | T3 M | 40° C. | 35.10 | 48.64 | 16.26 |

TABLE 13B

Chemical stability of Formulation 8 as determined by IEX.

| Formulation # | Time-point | Condition | % Acidic | % Zero | % Basic |
|---|---|---|---|---|---|
| 8 | Pre-Lyo | | 33.71 | 57.31 | 8.98 |
| PEG3350:Ab = 35:1 | T0 | T0 | 31.90 | 61.49 | 6.61 |
| Sorbitol:Ab = 55:1 | T1 M | 2-8° C. | 31.60 | 62.16 | 6.24 |
| | T3 M | 2-8° C. | 31.92 | 62.90 | 5.18 |
| | T1 M | 25° C. | 32.67 | 60.21 | 7.13 |
| | T3 M | 25° C. | 32.46 | 61.72 | 5.81 |
| | T1 M | 40° C. | 35.06 | 54.46 | 10.48 |
| | T2 M | 40° C. | | | |
| | T3 M | 40° C. | 36.89 | 49.93 | 16.26 |

TABLE 13C

Chemical stability of Formulation 26 as determined by IEX.

| Formulation # | Time-point | Condition | % Acidic | % Zero | % Basic |
|---|---|---|---|---|---|
| 26 | Pre-Lyo | | 36.72 | 53.87 | 9.40 |
| PEG3350:Ab = 10:1 | T0 | T0 | 36.38 | 57.33 | 6.28 |
| Sorbitol:Ab = 80:1 | T1 M | 2-8° C. | 38.63 | 54.56 | 6.82 |
| | T3 M | 2-8° C. | 38.48 | 55.17 | 6.35 |
| | T1 M | 25° C. | 38.21 | 55.03 | 6.76 |
| | T3 M | 25° C. | 38.39 | 55.18 | 6.43 |
| | T1 M | 40° C. | 38.02 | 52.75 | 9.23 |
| | T3 M | 40° C. | 39.38 | 47.54 | 13.08 |

TABLE 13D

Chemical stability of Formulation 27 as determined by IEX.

| Formulation # | Time-Point | Condition | % Acidic | % Zero | % Basic |
|---|---|---|---|---|---|
| 27 | Pre-Lyo | | 36.41 | 54.18 | 9.41 |
| PEG3350:Ab = 10:1 | T0 | T0 | 38.17 | 52.55 | 9.28 |
| Sorbitol:Ab = 631:1 | T1 M | 2-8° C. | 37.00 | 53.52 | 9.48 |
| | T3 M | 2-8° C. | 33.97 | 58.69 | 7.34 |
| | T1 M | 25° C. | 36.59 | 53.68 | 9.72 |
| | T3 M | 25° C. | 41.73 | 46.69 | 11.58 |

TABLE 13D-continued

Chemical stability of Formulation 27 as determined by IEX.

| Formulation # | Time-Point | Condition | % Acidic | % Zero | % Basic |
|---|---|---|---|---|---|
| | T1 M | 40° C. | 36.26 | 50.80 | 12.94 |
| | T3 M | 40° C. | 37.89 | 40.48 | 21.63 |

TABLE 13E

Chemical stability of Formulation 1 as determined by IEX.

| Formulation # | Time-point | Condition | % Acidic | % Zero | % Basic |
|---|---|---|---|---|---|
| 1 | | Pre-Lyo | 34.07 | 59.33 | 6.60 |
| | T0 | T0 | 32.15 | 57.93 | 9.92 |
| | T1 M | 2-8° C. | 32.55 | 59.39 | 8.05 |
| | T3 M | 2-8° C. | 29.41 | 59.44 | 11.15 |
| | T1 M | 25° C. | 29.28 | 58.68 | 12.03 |
| | T3 M | 25° C. | 29.28 | 58.68 | 12.03 |
| | T1 M | 40° C. | 31.16 | 56.92 | 11.92 |
| | T3 M | 40° C. | 29.20 | 55.89 | 14.91 |

Drug product lyophilized in 4 test formulations were stored at different conditions namely 2-8° C., 25° C.±2° C. (60%±5% R.H.) and 40° C.±2° C. (75%±5% R.H.) for a duration of 3 months and compared to drug product in the reference formulation (Formulation 1) also placed in the same storage conditions. Physical stability and chemical stability were monitored. Formulations that contained relatively higher proportion of sorbitol provided superior physical stability than those with lesser amount of sorbitol. In this regard, Formulation 27 ranked better than Formulation 26 and Formulation 6 ranked better than Formulation 8. Also relatively lesser proportion of PEG3350 afforded greater physical stability to the drug product. Based on physical stability, the formulations are ranked as: Form 27>Form 6>Form 26=Form 8.

Figure 10:
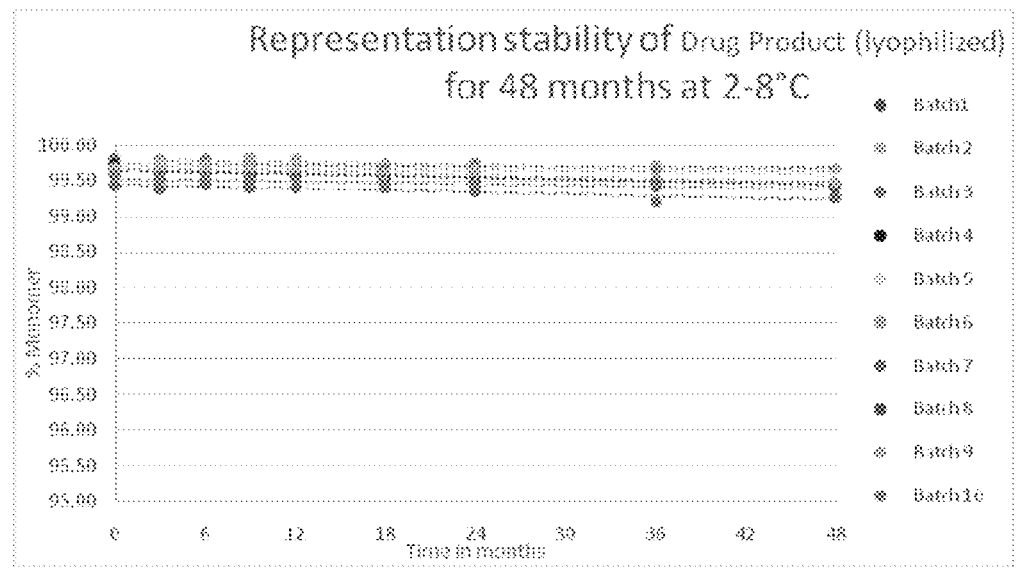
FIG. 10 depicts the comparable physical stability data of formulation identified as Formulation 27, as described herein, and subsequently lyophilized, in batches 1-10, when stored at 2-8° C. for 4 years (48 months).
Figure 11:
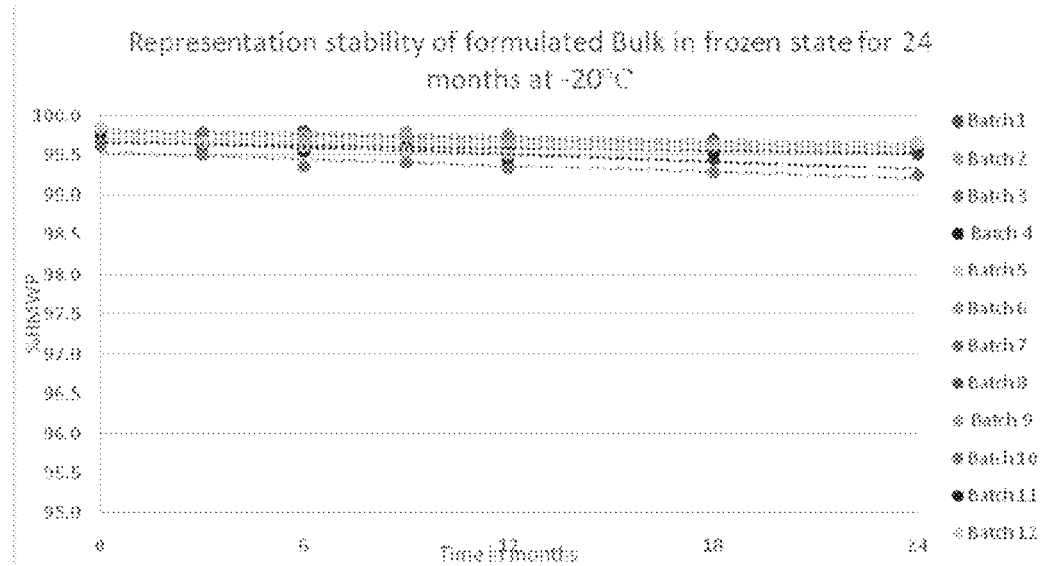
FIG. 11 depicts the comparable physical stability data of the protein drug formulations, as described herein, before lyophilization in batches 1-12, when stored at −20° C. for 2 years (24 months).

The FIGS. 10-11 represent comparable physical stability study data between the Lyophilized Formulation and Bulk drug formulation.

In one of the examples, the lyophilized formulation identified as Formulation 27 were taken in 12 batches namely Batch 1-Batch 12, and stored at 2-8° C. for a duration of at least 4 years. It was found that the formulation is stable for the four years (48 months) time as evident from FIG. 10.

In another example, the bulk drug formulation before lyophilization, identified in the Formulation 27 was also taken in 12 batches namely Batch 1 to 12 and the stability was ascertained on storage at −20° C. for a duration of 2 years, All the formulations showed stability for two years (24 months) at extreme conditions.

Thus the bulk drug and the lyophilized form were found to be are storage stable for at least two and four years respectively when stored at aforementioned mentioned conditions.

6. Formulation of the Bulk Drug Substance

In order to evaluate whether a sugar is required during the TFF step, the viral filtrate was formulated in the presence and absence of Sorbitol and the resultant drug substance was monitored via size exclusion chromatography (SEC) for any possible changes in the size variants distribution.

The drug substance after TFF into His./His. HCl buffer was subjected to Viral Filtration. The resulting viral filtrate at a concentration of ~30 mg/mL was formulated by addition of liquid stock solutions of 1M Sorbitol and 50 mM PEG 3350, prepared in His. His.HCl buffer to target a final concentration of 105.4 mM and 1.67 mM respectively. The final concentration of the bulk drug substance was adjusted to 25 mg/mL using His./His.HCl buffer and the pH was adjusted to 6.00±0.50 using 0.1N NaOH or 0.1N HCl as required.

Size variants data at each step indicate that TFF of the drug substance into a buffer that lacks sugar is not detrimental to the protein.

It is to be noted that the term "a" or "an" entity refers to one or more of that entity; for example, "an anti-HER2 antibody" is understood to represent one or more anti-HER2 antibodies. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A stable pharmaceutical formulation comprising an anti-HER2 antibody in a molar concentration of 0.10 mM to 0.25 mM, a sugar alcohol consisting of sorbitol, a histidine buffer comprising from 1.0 mM to 3.0 mM L-histidine and from 1.5 mM to 3.0 mM L-histidine hydrochloride and polyethylene glycol (PEG), wherein the PEG has a molecular weight from 2000 g/mol to 5000 g/mol and wherein the sorbitol and the anti-HER2 antibody is present in a molar ratio of 550 to 700 mole of sorbitol:1 mole of the anti-HER2 antibody; wherein the PEG is present in a molar ratio of 5 to 15 mole PEG:1 mole of the anti-HER2 antibody, wherein the stable pharmaceutical formulation has a pH of 5.0-7.5.

2. The formulation as claimed in claim 1, wherein the anti-HER2 antibody and sorbitol are present in a molar ratio of 660 mole of sorbitol:1 mole of antibody.

3. The formulation as claimed in claim 1 wherein PEG is PEG 3350.

4. The formulation as claimed in claim 1, wherein the molar concentration of sorbitol is about 90 mM to about 120 mM.

5. The formulation as claimed in claim 1, which is lyophilized or liquid formulation.

6. The formulation as claimed in claim 3 comprising the sorbitol, PEG 3350, the anti-HER2 antibody and histidine buffer, wherein the sorbitol to the anti-HER2 antibody is in molar ratio of 631:1 and PEG 3350 to the anti-HER2 antibody is in molar ratio of 10:1.

7. The formulation as claimed in claim 6 in a lyophilized form which is stable at 2-8° C. for at least 4 years.

8. The formulation as claimed in claim 1, wherein the formulation does not include either of sucrose or trehalose.

9. The formulation as claimed in claim 1, wherein the formulation further comprises L-methionine.

10. A process for preparing a stable formulation, comprising the steps of:
a) mixing an anti-HER2 antibody in a molar concentration of 0.10 mM to 0.25 mM and a sugar alcohol consisting of sorbitol in the molar ratio of 550-700 mole sorbitol:1 mole of the anti-HER2 antibody, a histidine buffer comprising from 1.0 mM to 3.0 mM L-histidine and from 1.5 mM to 3.0 mM L-histidine hydrochloride and polyethylene glycol PEG in the molar ratio of 5 to 15 mole PEG:1 mole of the anti-HER2 antibody, wherein the PEG has a molecular weight from 2000 g/mol to 5000 g/mol and wherein the stable formulation has a pH of 5.0-7.5;

b) lyophilizing the mixture; and optionally c) reconstituting the lyophilized mixture of step (b) in a diluent such that the anti-HER2 antibody concentration is from 5 mg/ml to 50 mg/ml.

11. The process as claimed in claim 10, wherein the lyophilized mixture further comprises a bulking agent.

12. A pharmaceutical kit comprising:

a) a container which holds a lyophilized mixture of an anti-HER2 antibody in a molar concentration of 0.10 mM to 0.25 mM, and a sugar alcohol consisting of sorbitol in a molar ratio of 550-700 mole sorbitol:1 mole of the anti-HER2 antibody, and polyethylene glycol PEG in a molar ratio of 5 to 15 mole PEG:1 mole of the anti-HER2 antibody, wherein the PEG has a molecular weight from 2000 g/ml to 5000 g/ml, wherein the mixture before lyophilization is buffered with a histidine buffer comprising from 1.0 mM to 3.0 mM L-histidine and from 1.5 mM to 3.0 mM L-histidine hydrochloride, wherein the mixture before lyophilization has a pH of 5.0-7.5; and b) instruction for reconstituting the lyophilized mixture with a diluent.

13. The pharmaceutical kit as claimed in claim 12, further comprising a second container which holds the diluent.

14. The pharmaceutical kit as claimed in claim 13, wherein the diluent is selected from sterile water for injection and bacteriostatic water for injection (BWFI) comprising an aromatic alcohol.

15. The pharmaceutical kit as claimed in claim 12, wherein the container is selected from multi-use vial and vial with stopper pierceable syringe.

16. The pharmaceutical kit as claimed in claim 12, wherein the lyophilized formulation is stable upon storage at 2-8° C. for at least 4 years.

17. The pharmaceutical kit as claimed in claim 12, wherein the anti-HER2 antibody is trastuzumab.

* * * * *